(12) United States Patent
Waldman et al.

(10) Patent No.: US 9,662,405 B2
(45) Date of Patent: May 30, 2017

(54) METHOD OF TREATING CANCER BY ADMINISTERING CHIMERIC ANTIGEN RECEPTOR COMPRISING ANTI-GCC ANTIBODY

(71) Applicant: Thomas Jefferson University, Philadelphia, PA (US)

(72) Inventors: Scott A. Waldman, Ardmore, PA (US); Michael S. Magee, Philadelphia, PA (US); Adam E. Snook, Aston, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 14/879,936

(22) Filed: Oct. 9, 2015

(65) Prior Publication Data

US 2016/0030595 A1  Feb. 4, 2016

Related U.S. Application Data

(62) Division of application No. 13/872,065, filed on Apr. 26, 2013, now Pat. No. 9,156,915.

(60) Provisional application No. 61/638,639, filed on Apr. 26, 2012.

(51) Int. Cl.
| | | |
|---|---|---|
| *A61K 39/395* | (2006.01) | |
| *A61K 47/48* | (2006.01) | |
| *C07K 16/40* | (2006.01) | |
| *G01N 33/574* | (2006.01) | |
| *G01N 33/573* | (2006.01) | |
| *A61K 49/00* | (2006.01) | |
| *A61K 51/10* | (2006.01) | |
| *A61K 35/17* | (2015.01) | |

(52) U.S. Cl.
CPC ........ *A61K 47/48646* (2013.01); *A61K 35/17* (2013.01); *A61K 47/48384* (2013.01); *A61K 47/48615* (2013.01); *A61K 49/0058* (2013.01); *A61K 51/1063* (2013.01); *A61K 51/1075* (2013.01); *C07K 16/40* (2013.01); *G01N 33/573* (2013.01); *G01N 33/57492* (2013.01); *C07K 2317/622* (2013.01); *G01N 2333/988* (2013.01)

(58) Field of Classification Search
CPC .............. A61K 35/17; A61K 47/48615; A61K 47/48646
See application file for complete search history.

(56) References Cited

U.S. PATENT DOCUMENTS

| | | |
|---|---|---|
| 3,940,475 A | 2/1976 | Gross |
| 4,179,337 A | 12/1979 | Davis et al. |
| 4,289,747 A | 9/1981 | Chu |
| 4,376,110 A | 3/1983 | David et al. |
| 4,486,414 A | 12/1984 | Pettit |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,816,397 A | 3/1989 | Boss et al. |
| 4,816,444 A | 3/1989 | Pettit et al. |
| 4,816,567 A | 3/1989 | Cabilly et al. |
| 4,868,103 A | 9/1989 | Stavrianopoulos et al. |
| 4,879,278 A | 11/1989 | Pettit et al. |
| 4,978,744 A | 12/1990 | Pettit et al. |
| 4,986,988 A | 1/1991 | Pettit et al. |
| 5,076,973 A | 12/1991 | Pettit et al. |
| 5,101,827 A | 4/1992 | Goldenberg |
| 5,102,990 A | 4/1992 | Rhodes |
| 5,138,036 A | 8/1992 | Pettit et al. |
| 5,194,594 A | 3/1993 | Khawli et al. |
| 5,208,020 A | 5/1993 | Chari et al. |
| 5,225,539 A | 7/1993 | Winter |
| 5,229,275 A | 7/1993 | Goroff |
| 5,410,024 A | 4/1995 | Pettit et al. |
| 5,504,191 A | 4/1996 | Pettit et al. |
| 5,518,888 A | 5/1996 | Waldman |
| 5,521,284 A | 5/1996 | Pettit et al. |
| 5,530,097 A | 6/1996 | Pettit et al. |
| 5,530,101 A | 6/1996 | Queen et al. |
| 5,554,725 A | 9/1996 | Pettit |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,599,902 A | 2/1997 | Pettit et al. |

(Continued)

FOREIGN PATENT DOCUMENTS

| | | |
|---|---|---|
| EP | 519596 A1 | 12/1992 |
| GB | 2209757 A | 5/1989 |

(Continued)

OTHER PUBLICATIONS

Babcook et al., "A novel strategy for generating monoclonal antibodies from single, isolated lymphocytes producing antibodies of defined specificities" Proc Natl Acad Sci USA (1996) 93:7843-7848.

Bakre et al., "Homologous desensitization of the human guanylate cyclase C receptor. Cell-specific regulation of catalytic activity," Eur. J. Biochem. (2000) 267:179-187.

Blakey et al., ZD2767, an improved system for antibody-directed enzyme prodrug therapy that results in tumor regressions in colorectal tumor xenografts, Cancer Res. (1996) 56(14):3287-3292.

Brown et al. Tolerance to Single, but Not Multiple, Amino Acid Replacements in Antibody V, CDR2. Journal of Immunology. May 1996;156(9):3285-91.

(Continued)

*Primary Examiner* — Prema Mertz
(74) *Attorney, Agent, or Firm* — Pepper Hamilton LLP

(57) ABSTRACT

Antibodies and antigen-binding fragments of antibodies that bind GCC are disclosed. In some embodiments, the antibodies are humanized, chimeric or human. Nucleic acids and vectors encoding the antibodies or portions thereof, recombinant cells that contain the nucleic acids, and compositions comprising the antibodies or antigen-binding fragments are also disclosed. The invention also provides therapeutic and diagnostic methods utilizing the antibodies and antigen-binding.

5 Claims, No Drawings

(56) References Cited

U.S. PATENT DOCUMENTS

| | | |
|---|---|---|
| 5,601,990 A | 2/1997 | Waldman |
| 5,612,460 A | 3/1997 | Zalipsky |
| 5,622,929 A | 4/1997 | Willner et al. |
| 5,624,821 A | 4/1997 | Winter et al. |
| RE35,500 E | 5/1997 | Rhodes |
| 5,627,052 A | 5/1997 | Schrader |
| 5,631,169 A | 5/1997 | Lakowicz et al. |
| 5,635,483 A | 6/1997 | Pettit et al. |
| 5,648,260 A | 7/1997 | Winter et al. |
| 5,648,471 A | 7/1997 | Buttram et al. |
| 5,663,149 A | 9/1997 | Pettit et al. |
| 5,665,860 A | 9/1997 | Pettit et al. |
| 5,693,761 A | 12/1997 | Queen et al. |
| 5,693,792 A | 12/1997 | Torii et al. |
| 5,697,902 A | 12/1997 | Goldenberg |
| 5,714,350 A | 2/1998 | Co et al. |
| 5,741,957 A | 4/1998 | Deboer et al. |
| 5,750,172 A | 5/1998 | Meade et al. |
| 5,756,687 A | 5/1998 | Denman et al. |
| 5,777,085 A | 7/1998 | Co et al. |
| 5,780,588 A | 7/1998 | Pettit et al. |
| 5,827,690 A | 10/1998 | Meade et al. |
| 5,834,597 A | 11/1998 | Tso et al. |
| 5,871,907 A | 2/1999 | Winter et al. |
| 5,916,771 A | 6/1999 | Hori et al. |
| 6,020,153 A | 2/2000 | Hardman et al. |
| 6,034,065 A | 3/2000 | Pettit et al. |
| 6,057,098 A | 5/2000 | Buechler et al. |
| 6,239,104 B1 | 5/2001 | Pettit et al. |
| 6,300,064 B1 | 10/2001 | Knappik et al. |
| 6,323,315 B1 | 11/2001 | Pettit et al. |
| 6,331,415 B1 | 12/2001 | Cabilly et al. |
| 6,333,410 B1 | 12/2001 | Chari et al. |
| 6,767,704 B2 | 7/2004 | Waldman et al. |
| 6,884,869 B2 | 4/2005 | Senter et al. |
| 7,091,186 B2 | 8/2006 | Senter et al. |
| 7,317,091 B2 | 1/2008 | Lazar et al. |
| 7,498,298 B2 | 3/2009 | Doronina et al. |
| 2003/0026805 A1 | 2/2003 | Athwal et al. |
| 2003/0083236 A1 | 5/2003 | Petrov et al. |
| 2003/0157108 A1 | 8/2003 | Presta |
| 2004/0093621 A1 | 5/2004 | Shitara et al. |
| 2004/0258687 A1 | 12/2004 | Waldman et al. |
| 2005/0009751 A1 | 1/2005 | Senter et al. |
| 2005/0037421 A1 | 2/2005 | Honda et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2006/0147445 A1 | 7/2006 | O'Keefe et al. |
| 2008/0300192 A1 | 12/2008 | Doronina et al. |
| 2009/0010945 A1 | 1/2009 | Alley et al. |

FOREIGN PATENT DOCUMENTS

| | | |
|---|---|---|
| WO | 8907142 A1 | 8/1989 |
| WO | 9404678 A1 | 3/1994 |
| WO | 9429351 A2 | 12/1994 |
| WO | 9506058 A1 | 3/1995 |
| WO | 9852976 A1 | 11/1998 |
| WO | 0026256 A2 | 5/2000 |
| WO | 0034317 A2 | 6/2000 |
| WO | 0042072 A2 | 7/2000 |
| WO | 02088172 A2 | 11/2002 |
| WO | 03014161 A2 | 2/2003 |
| WO | 2004010957 A2 | 2/2004 |
| WO | 2011066048 A1 | 6/2011 |

OTHER PUBLICATIONS

Chari et al., "Immunoconjugates containing novel maytansinoids: promising anticancer drugs.," J Med Chem (1992) 52:127-131.

Holliger et al., ""Diabodies": small bivalent and bispecific antibody fragments," Proc Natl Acad Sci USA (1993) 90:6444-6448.

Huston et al., "Protein engineering of antibody binding sites: recovery of specific activity in an anti-digoxin single-chain Fv analogue produced in *Escherichia coli*," Proc Natl Acad Sci USA (1988) 85:5879-5883.

Lazar et al., "Engineered antibody Fc variants with enhanced effector function," Proc Natl Acad Sci USA (2006) 103:4005-4010.

Nandi et al., "Topological mimicry and epitope duplication in the guanylyl cyclase C receptor," Protein Sci. (1998) 7:2175-2183.

Rudikoff et al. Single amino acid substitution altering antigen-binding specificity. Proceeding of the National Academy of Sciences. Mar. 1982; 79(6):1979-1983.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem (2001) 276:6591-6604.

Vajdos et al. Comprehensive Functional Maps of the Antigen binding Site of an Anti-ErbB2 Antibody Obtained with Shotgun Scanning Mutagenesis. Journal ofMolecular Biology. Jul. 5, 2002; 320(2):415-28.

Valentino et al. A uroguanylin-GUCY2C endocrine axis regulates feeding in mice. Journal of Clinical Investigation. 2011; 121(9): 3578-3588.

SEQUENCE LISTING

```
<160> NUMBER OF SEQ ID NOS: 4

<210> SEQ ID NO 1
<211> LENGTH: 121
<212> TYPE: PRT
<213> ORGANISM: Mouse

<400> SEQUENCE: 1

Glu Val Met Leu Val Glu Ser Gly Gly Gly Leu Val Lys Pro Gly Gly
```

-continued

```
  1               5                   10                  15
Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
            35                  40                  45

Ala Thr Ile Thr Ser Gly Gly Ser Tyr Thr Tyr Tyr Pro Asp Ser Val
            50                  55                  60

Lys Gly Arg Phe Thr Ile Ser Arg Asp Asn Ala Lys Asn Ile Leu Tyr
 65                  70                  75                  80

Leu Gln Met Ser Ser Leu Arg Ser Glu Asp Thr Ala Met Tyr Tyr Cys
                85                  90                  95

Thr Arg Leu Arg Gln Ile Gly Leu Arg Gly Phe Ser Asp Tyr Trp Gly
                    100                 105                 110

Gln Gly Thr Thr Leu Thr Val Ser Ser
            115                 120
```

<210> SEQ ID NO 2
<211> LENGTH: 109
<212> TYPE: PRT
<213> ORGANISM: Mouse

<400> SEQUENCE: 2

```
Asp Ile Asp Ile Leu Met Thr Gln Ser Pro Ser Ser Met Tyr Ala Ser
 1               5                   10                  15

Leu Gly Glu Arg Val Thr Ile Thr Cys Lys Ala Ser His Asp Ile Lys
            20                  25                  30

Ser Tyr Leu Ser Trp Tyr Gln Gln Lys Pro Trp Arg Ser Pro Lys Thr
            35                  40                  45

Leu Ile Tyr Tyr Thr Thr Ala Leu Ala Asp Gly Val Pro Ser Arg Phe
            50                  55                  60

Ser Gly Ser Gly Ser Gly Gln Asp Tyr Ser Leu Thr Ile Ser Ser Leu
 65                  70                  75                  80

Glu Ser Asp Asp Thr Ala Thr Tyr Tyr Cys Leu Gln His Gly Glu Ser
                85                  90                  95

Pro Tyr Thr Phe Gly Gly Gly Thr Lys Leu Glu Ile Lys
                    100                 105
```

<210> SEQ ID NO 3
<211> LENGTH: 119
<212> TYPE: PRT
<213> ORGANISM: Mouse

<400> SEQUENCE: 3

```
Glu Val Gln Leu Glu Glu Ser Gly Pro Glu Leu Val Lys Pro Gly Ala
 1               5                   10                  15

Ser Val Lys Met Ser Cys Lys Ala Ser Gly Tyr Thr Phe Thr Asp Tyr
            20                  25                  30

Val Ile Ser Trp Val Lys Gln Thr Gly Gln Gly Leu Glu Trp Ile
            35                  40                  45

Gly Val Thr Tyr Pro Gly Ser Gly Asn Thr Tyr Tyr Gly Glu Arg Phe
            50                  55                  60

Lys Gly Lys Ala Thr Leu Thr Val Asp Lys Met Ser Asn Thr Ala Tyr
 65                  70                  75                  80

Met Gln Leu Ser Ser Leu Thr Ser Glu Asp Ser Ala Val Tyr Phe Cys
                85                  90                  95

Thr Arg Asn Tyr Gly Ser Phe Tyr Ala Leu Asp Tyr Trp Gly Gln Gly
```

```
                        100                 105                 110
Thr Ser Val Thr Val Ser Ser
            115

<210> SEQ ID NO 4
<211> LENGTH: 108
<212> TYPE: PRT
<213> ORGANISM: Mouse

<400> SEQUENCE: 4

Asp Ile Asp Ile Leu Met Thr Gln Ser Pro Ala Thr Leu Ser Val Thr
1               5                   10                  15

Pro Gly Asp Arg Val Ser Leu Ser Cys Arg Ala Ser Gln Ser Ile Arg
            20                  25                  30

Asp Tyr Leu His Trp Tyr Gln His Arg Ser His Glu Ser Pro Arg Leu
        35                  40                  45

Leu Ile Lys Tyr Ala Ser Gln Ser Ile Ser Gly Ile Pro Ser Arg Phe
    50                  55                  60

Ser Gly Ser Gly Ser Gly Ser Asp Phe Thr Leu Thr Ile Asn Ser Val
65                  70                  75                  80

Glu Pro Glu Asp Val Gly Val Tyr Tyr Cys Gln Asn Gly His Ser Phe
                85                  90                  95

Pro Thr Phe Gly Gly Gly Thr Lys Leu Glu Ile Lys
                100                 105
```

METHOD OF TREATING CANCER BY ADMINISTERING CHIMERIC ANTIGEN RECEPTOR COMPRISING ANTI-GCC ANTIBODY

CROSS-REFERENCE TO RELATED APPLICATIONS

This application is a Divisional application of U.S. patent application Ser. No. 13/872,065, which is a U.S. Non-Provisional application, which claims priority to U.S. Provisional Application No. 61/638,639 filed Apr. 26, 2012, which is incorporated herein by reference in its entirety.

FIELD OF THE INVENTION

Antibody molecules that bind to human guanylyl cyclase C are provided including compounds and compositions which comprise such antibodies and methods of making and using the same.

BACKGROUND OF THE INVENTION

Guanylyl cyclase C (GCC) (also known as STAR, ST Receptor, GUC2C, and GUCY2C) is a transmembrane cell surface receptor that functions in the maintenance of intestinal fluid, electrolyte homeostasis and cell proliferation (Carrithers et al., Proc Natl Acad Sci USA 100: 3018-3020 (2003); Mann et al., Biochem Biophys Res Commun 239: 463-466 (1997); Pitari et al., Proc Natl Acad Sci USA 100: 2695-2699 (2003)); GenBank Accession No. NM.sub.—004963, each of which is incorporated herein by reference). This function is mediated through binding of guanylin (Wiegand et al. FEBS Lett. 311:150-154 (1992)). GCC also is a receptor for heat-stable enterotoxin which is a peptide produced by *E. coli*, as well as other infectious organisms (Rao, M. C. Ciba Found. Symp. 112:74-93 (1985); Knoop F. C. and Owens, M. J. Pharmacol. Toxicol. Methods 28:67-72 (1992)). Binding of ST to GCC activates a signal cascade that results in enteric disease, e.g., diarrhea.

GCC is expressed at the mucosal cells lining the small intestine, large intestine and rectum (Carrithers et al., Dis Colon Rectum 39: 171-181 (1996)). GCC expression is maintained upon neoplastic transformation of intestinal epithelial cells, with expression in all primary and metastatic colorectal tumors (Carrithers et al., Dis Colon Rectum 39: 171-181 (1996); Buc et al. Eur J Cancer 41: 1618-1627 (2005); Carrithers et al., Gastroenterology 107: 1653-1661 (1994)). GCC expression has also been detected in esophageal cells diagnosed as Barrett's esophagus, esophageal cancer and gastric cancer.

The tissue-specific expression and association with cancer, e.g., of gastrointestinal origin, (e.g., colon cancer, stomach cancer, or esophageal cancer), can be exploited for the use of GCC as a diagnostic marker for this disease (Carrithers et al., Dis Colon Rectum 39: 171-181 (1996); Buc et al. Eur J Cancer 41: 1618-1627 (2005)).

Cancer is a leading cause of death worldwide, accounting for >7 million deaths each year. Cancer mortality is nearly universally related to the spread of primary tumors to distant sites forming metastases and ultimately leading to death. This is particularly true for colorectal cancer in which an inverse relationship exists between disease spread and prognosis. Guanylyl Cyclase C (GCC) is a member of the particulate family of guanylyl cyclases and is found selectively on the apical surfaces of intestinal epithelial cells. Importantly its expression is maintained on 100% of differentiated primary metastatic tumors arising from the colon and can be targeted for diagnostic and therapeutic purposes. The advent of monoclonal antibody (mAb) technology has made a prodigious impact on biochemical and immunoassays as well as cancer therapeutics and diagnostics.

As a cell surface protein, GCC can also serve as a therapeutic target for receptor binding proteins such as antibodies or ligands. In normal intestinal tissue, GCC is expressed on the apical side of epithelial cell tight junctions that form an impermeable barrier between the luminal environment and vascular compartment (Almenoff et al., Mol Microbiol 8: 865-873); Guarino et al., Dig Dis Sci 32: 1017-1026 (1987)). As such, systemic intravenous administration of a GCC-binding protein therapeutic will have minimal effect on intestinal GCC receptors, while having access to neoplastic cells of the gastrointestinal system, including invasive or metastatic colon cancer cells, extraintestinal or metastatic colon tumors, esophageal tumors or stomach tumors, adenocarcinoma at the gastroesophageal junction. Additionally, GCC internalizes through receptor mediated endocytosis upon ligand binding (Buc et al. Eur J Cancer 41: 1618-1627 (2005); Urbanski et al., Biochem Biophys Acta 1245: 29-36 (1995)).

Polyclonal antibodies raised against the extracellular domain of GCC (Nandi et al. Protein Expr. Purif. 8:151-159 (1996)) were able to inhibit the ST peptide binding to human and rat GCC and inhibit ST-mediated cGMP production by human GCC.

GCC has been characterized as a protein involved in cancers, including colon cancers. See also, Carrithers et al., Dis Colon Rectum 39: 171-181 (1996); Buc et al. Eur J Cancer 41: 1618-1627 (2005); Carrithers et al., Gastroenterology 107: 1653-1661 (1994); Urbanski et al., Biochem Biophys Acta 1245: 29-36 (1995).

A nucleotide sequence for human GCC is disclosed as GenBank Accession No. NM.sub.—004963, which is incorporated herein by reference.

Amino acid sequence for human GCC is disclosed as GenPept Accession No. NP.sub.—004954, which is incorporated herein by reference.

Monoclonal antibodies specific for GCC include GCC:B10 (Nandi et al., J. Cell. Biochem. 66:500-511 (1997)), GCC:4D7 (Vijayachandra et al. Biochemistry 39:16075-16083 (2000)) and GCC:C8 (Bakre et al. Eur. J. Biochem. 267:179-187 (2000)). GCC:B10 has a kappa light chain and an IgG2a isotype and cross-reacts to rat, pig and monkey GCC. GCC:B10 binds to the first 63 amino acids of the intracellular domain of GCC (Nandi et al. Protein Sci. 7:2175-2183 (1998)). GCC:4D7 binds to the kinase homology domain, within residues 491-568 of GCC (Bhandari et al. Biochemistry 40:9196-9206 (2001)). GCC:C8 binds to the protein kinase-like domain in the cytoplasmic portion of GCC.

U.S. Pat. No. 5,518,888, which is incorporated herein by reference, discloses compositions including anti-GCC antibodies which in some embodiments may be conjugated to active agents. Methods using the compositions are disclosed including methods of imaging and methods of treating metastatic colorectal cancer.

U.S. Pat. No. 5,601,990 and patents and applications claiming common priority, which are each incorporated herein by reference, disclose methods using anti-GCC antibodies including methods diagnosing colorectal cancer, methods of determining the origin of adenocarcinomas of unconfirmed origin and methods of detecting the extent of primary colorectal tumor invasion of the intestinal/colon wall.

U.S. Pat. No. 5,518,888 and patents and applications claiming common priority, which are each incorporated herein by reference, disclose compositions including anti-GCC antibodies which in some embodiments may be conjugated to active agents. Methods using the compositions are disclosed including methods of imaging and methods of treating metastatic colorectal cancer.

U.S. Pat. No. 6,767,704 and patents and applications claiming common priority, which are each incorporated herein by reference, disclose methods using anti-GCC antibodies including methods diagnosing, imaging and treating primary and metastatic esophageal and stomach cancer.

PCT application PCT/US10/053733 and provisional applications 61/107,613 and 61/254,119, which are each incorporated herein by reference, disclose T cells which express fusion proteins that comprise an anti-GCC antibody portion on the cell surface and methods of making and using such T cells.

DESCRIPTION OF PREFERRED EMBODIMENTS

As used herein, the term "antibody molecule" refers to an antibody, antibody peptide(s) or immunoglobulin, or an antigen binding fragment of any of the foregoing, e.g., of an antibody. Antibody molecules include single chain antibody molecules, e.g., scFv, see. e.g., Bird et al. (1988) Science 242:423-426; and Huston et al. (1988) Proc. Natl. Acad. Sci. USA 85:5879-5883), and single domain antibody molecules, see, e.g., WO9404678. Although not within the term "antibody molecules," the invention also includes "antibody analog(s)," other non-antibody molecule protein-based scaffolds, e.g., fusion proteins and/or immunoconjugates that use CDRs to provide specific antigen binding.

An "anti-GCC antibody molecule" refers to an antibody molecule (i.e., an antibody, antigen-binding fragment of an antibody or antibody analog) which interacts with or recognizes, e.g., binds (e.g., binds specifically) to GCC, e.g., human GCC.

As used herein, the term "antibody," "antibody peptide(s)" or "immunoglobulin" refers to single chain, two-chain, and multi-chain proteins and glycoproteins. The term antibody includes polyclonal, monoclonal, chimeric, CDR-grafted and human or humanized antibodies, all of which are discussed in more detail elsewhere herein. Also included within the term are camelid antibodies, see, e.g., US2005/0037421, and nanobodies, e.g., IgNARs (shark antibodies), see, e.g., WO03/014161. The term "antibody" also includes synthetic and genetically engineered variants.

As used herein, the term "antibody fragment" or "antigen binding fragment" of an antibody refers, e.g., to Fab, Fab', F(ab')$_2$, and Fv fragments, single chain antibodies, functional heavy chain antibodies (nanobodies), as well as any portion of an antibody having specificity toward at least one desired epitope, that competes with the intact antibody for specific binding (e.g., a fragment having sufficient CDR sequences and having sufficient framework sequences so as to bind specifically to an epitope). E.g., an antigen binding fragment can compete for binding to an epitope which binds the antibody from which the fragment was derived. Derived, as used in this and similar contexts, does not imply any particular method or process of derivation, but can refer merely to sequence similarity. Antigen binding fragments can be produced by recombinant techniques, or by enzymatic or chemical cleavage of an intact antibody. The term, antigen binding fragment, when used with a single chain, e.g., a heavy chain, of an antibody having a light and heavy chain means that the fragment of the chain is sufficient such that when paired with a complete variable region of the other chain, e.g., the light chain, it will allow binding of at least 25, 50, 75, 85 or 90% of that seen with the whole heavy and light variable region.)

The term, "antigen binding constellation of CDRs" or "a number of CDRs sufficient to allow binding" (and similar language), as used herein, refers to sufficient CDRs of a chain, e.g., the heavy chain, such that when placed in a framework and paired with a complete variable region of the other chain, or with a portion of the other chain's variable region of similar length and having the same number of CDRs, e.g., the light chain, will allow binding, e.g., of at least 25, 50, 75, 85 or 90% of that seen with the whole heavy and light variable region.

As used herein, the term "human antibody" includes an antibody that possesses a sequence that is derived from a human germ-line immunoglobulin sequence, such as an antibody derived from transgenic mice having human immunoglobulin genes (e.g., XENOMOUSE™ genetically engineered mice (Abgenix, Fremont, Calif.)), human phage display libraries, human myeloma cells, or human B cells.

As used herein, the term "humanized antibody" refers to an antibody that is derived from a non-human antibody e.g., rodent (e.g., murine) that retains or substantially retains the antigen-binding properties of the parent antibody but is less immunogenic in humans. Humanized as used herein is intended to include deimmunized antibodies. Typically humanized antibodies include non-human CDRs and human or human derived framework and constant regions.

The term "modified" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse, sheep or goat) that is transgenic for human immunoglobulin genes or antibodies prepared, expressed, created or isolated by any other means that involves splicing of human immunoglobulin gene sequences to other DNA sequences. Such modified antibodies include humanized, CDR grafted (e.g., an antibody having CDRs from a first antibody and a framework region from a different source, e.g., a second antibody or a consensus framework), chimeric, in vitro generated (e.g., by phage display) antibodies, and may optionally include variable or constant regions derived from human germline immunoglobulin sequences or human immunoglobulin genes or antibodies which have been prepared, expressed, created or isolated by any means that involves splicing of human immunoglobulin gene sequences to alternative immunoglobulin sequences. In embodiments a modified antibody molecule includes an antibody molecule having a sequence change from a reference antibody.

The term "monospecific antibody" refers to an antibody or antibody preparation that displays a single binding specificity and affinity for a particular epitope. This term includes a "monoclonal antibody" or "monoclonal antibody composition."

The term "bispecific antibody" or "bifunctional antibody" refers to an antibody that displays dual binding specificity for two epitopes, where each binding site differs and recognizes a different epitope.

The terms "non-conjugated antibody" and "naked antibody" are used interchangeably to refer to an antibody molecule that is not conjugated to a non-antibody moiety, e.g., a therapeutic agent or a label.

The terms "immunoconjugate", "antibody conjugate", "antibody drug conjugate", and "ADC" are used interchangeably and refer to an antibody that is conjugated to a non-antibody moiety, e.g., a therapeutic agent or a label.

The term "agent" is used herein to denote a chemical compound, a mixture of chemical compounds, a biological macromolecule, or an extract made from biological materials. The term "therapeutic agent" refers to an agent that has biological activity.

The term "anti-cancer agent" or "chemotherapeutic agent" is used herein to refer to agents that have the functional property of inhibiting a development or progression of a neoplasm in a human, particularly a malignant (cancerous) lesion, such as a carcinoma, sarcoma, lymphoma, or leukemia Inhibition of metastasis or angiogenesis is frequently a property of anti-cancer or chemotherapeutic agents. A chemotherapeutic agent may be a cytotoxic or cytostatic agent. The term "cytostatic agent" refers to an agent which inhibits or suppresses cell growth and/or multiplication of cells.

"Cytotoxic agents" refer to compounds which cause cell death primarily by interfering directly with the cell's functioning, including, but not limited to, alkylating agents, tumor necrosis factor inhibitors, intercalators, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment of the invention and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody or antigen binding fragment of the invention.

As used herein the phrase, a sequence "derived from" or "specific for a designated sequence" refers to a sequence that comprises a contiguous sequence of approximately at least 6 nucleotides or at least 2 amino acids, at least about 9 nucleotides or at least 3 amino acids, at least about 10-12 nucleotides or 4 amino acids, or at least about 15-21 nucleotides or 5-7 amino acids corresponding, i.e., identical or complementary to, e.g., a contiguous region of the designated sequence. In certain embodiments, the sequence comprises all of a designated nucleotide or amino acid sequence. The sequence may be complementary (in the case of a polynucleotide sequence) or identical to a sequence region that is unique to a particular sequence as determined by techniques known in the art. Regions from which sequences may be derived, include but are not limited to, regions encoding specific epitopes, regions encoding CDRs, regions encoding framework sequences, regions encoding constant domain regions, regions encoding variable domain regions, as well as non-translated and/or non-transcribed regions. The derived sequence will not necessarily be derived physically from the sequence of interest under study, but may be generated in any manner, including, but not limited to, chemical synthesis, replication, reverse transcription or transcription, that is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified or combined in ways known in the art to be consistent with the intended use. For example, a sequence may comprise two or more contiguous sequences which each comprise part of a designated sequence, and are interrupted with a region which is not identical to the designated sequence but is intended to represent a sequence derived from the designated sequence. With regard to antibody molecules, "derived therefrom" includes an antibody molecule which is functionally or structurally related to a comparison antibody, e.g., "derived therefrom" includes an antibody molecule having similar or substantially the same sequence or structure, e.g., having the same or similar CDRs, framework or variable regions. "Derived therefrom" for an antibody also includes residues, e.g., one or more, e.g., 2, 3, 4, 5, 6 or more residues, which may or may not be contiguous, but are defined or identified according to a numbering scheme or homology to general antibody structure or three-dimensional proximity, i.e., within a CDR or a framework region, of a comparison sequence. The term "derived therefrom" is not limited to physically derived therefrom but includes generation by any manner, e.g., by use of sequence information from a comparison antibody to design another antibody.

As used herein, the phrase "encoded by" refers to a nucleic acid sequence that codes for a polypeptide sequence, wherein the polypeptide sequence or a portion thereof contains an amino acid sequence of at least 3 to 5 amino acids, at least 8 to 10 amino acids, or at least 15 to 20 amino acids from a polypeptide encoded by the nucleic acid sequence.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 30%, 40%, or 50%, at least 60%, or at least 70%, 80%, 90%, 95%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences can be determined using any method known in the art. For example, the Needleman and Wunsch, J. Mol. Biol. 48:444-453 (1970), algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. The percent homology between two nucleotide sequences can also be determined using the GAP program in the GCG software package (Accelerys, Inc. San Diego, Calif.), using an NWSgapdna.CMP matrix and a gap weight of 40, 50, 60, 70, or 80 and a length weight of 1, 2, 3, 4, 5, or 6. An exemplary set of parameters for determination of homology are a Blossum 62 scoring matrix with a gap penalty of 12, a gap extend penalty of 4, and a frameshift gap penalty of 5.

As used herein, the term "hybridizes under stringent conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45.degree. C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C. Very high stringency conditions (4) are often the preferred conditions and the ones that should be used unless otherwise specified.

It is understood that the antibodies and antigen binding fragment thereof of the invention may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie, J U et al. Science 247:1306-1310 (1990) or Padlan et al. FASEB J. 9:133-139 (1995). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or, without substantially altering a biological activity, whereas an "essential" amino acid residue results in such a change. In an antibody, an essential amino acid residue can be a specificity determining residue (SDR).

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, e.g., a mixture, solution or suspension or comprising an isolated cell or a cultured cell which comprises the polynucleotide or polypeptide, and still be isolated in that the vector or composition is not part of its natural environment.

As used herein, the term "replicon" refers to any genetic element, such as a plasmid, a chromosome or a virus, that behaves as an autonomous unit of polynucleotide replication within a cell.

As used herein, the term "operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

As used herein, the term "vector" refers to a replicon in which another polynucleotide segment is attached, such as to bring about the replication and/or expression of the attached segment.

As used herein, the term "control sequence" refers to a polynucleotide sequence that is necessary to effect the expression of a coding sequence to which it is ligated. The nature of such control sequences differs depending upon the host organism. In prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

As used herein, the term "purified product" refers to a preparation of the product which has been isolated from the cellular constituents with which the product is normally associated and/or from other types of cells that may be present in the sample of interest.

As used herein, the term "epitope" refers to a protein determinate capable of binding specifically to an antibody. Epitopic determinants usually consist of chemically active surface groupings of molecules such as amino acids or sugar side chains and usually have specific three dimensional structural characteristics, as well as specific charge characteristics. Some epitopes are linear epitopes while others are conformational epitopes. A linear epitope is an epitope wherein a contiguous amino acid primary sequence comprises the epitope recognized. A linear epitope typically includes at least 3, and more usually, at least 5, for example, about 8 to about 10 contiguous amino acids. A conformational epitope can result from at least two situations, such as: a) a linear sequence which is only exposed to antibody binding in certain protein conformations, e.g., dependent on ligand binding, or dependent on modification (e.g., phosphorylation) by signaling molecules; or b) a combination of structural features from more than one part of the protein, or in multisubunit proteins, from more than one subunit, wherein the features are in sufficiently close proximity in 3-dimensional space to participate in binding.

As used herein, "isotype" refers to the antibody class (e.g., IgM or IgG1) that is encoded by heavy chain constant region genes.

As used herein, the terms "detectable agent," "label" or "labeled" are used to refer to incorporation of a detectable marker on a polypeptide or glycoprotein. Various methods of labeling polypeptides and glycoproteins are known in the art and may be used. Examples of labels for polypeptides include, but are not limited to, the following: radioisotopes or radionuclides (e.g., indium (111In), iodine (131I or 125I), yttrium (90Y), lutetium (177Lu), actinium (225Ac), bismuth (212Bi or 213Bi), sulfur (35S), carbon (14C), tritium (3H), rhodium (188Rh), technetium (99 mTc), praseodymium, or phosphorous (32P) or a positron-emitting radionuclide, e.g., carbon-11 (11C), potassium-40 (40K), nitrogen-13 (13N), oxygen-15 (15O)9 fluorine-18 (18F), and iodine-121 (121I)), fluorescent labels (e.g., FITC, rhodamine, lanthanide phosphors), enzymatic labels (e.g., horseradish peroxidase, beta-galactosidase, luciferase, alkaline phosphatase), chemiluminescent, biotinyl groups (which can be detected by a marked avidin, e.g., a molecule containing a streptavidin moiety and a fluorescent marker or an enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "specific binding," "bind(s) specifically" or "binding specificity" means, for an anti-GCC antibody molecule, that the antibody molecule binds to GCC, e.g., human GCC protein, with greater affinity than it does to a non-GCC protein, e.g., BSA. Typically an anti-GCC molecule will have a $K_d$ for the non-GCC protein, e.g., BSA, which is greater than 2, greater than 10, greater than 100, greater than 1,000 times, greater than $10^4$, greater than $10^5$ or greater than $10^6$ times its Kd for GCC, e.g., human GCC protein. In determination of Kd, the Kd for GCC and the non-GCC protein, e.g., BSA, should be done under the same conditions.

As used herein, the term "treat" or "treatment" is defined as the administration of an anti-GCC antibody molecule to a subject, e.g., a patient, or administration, e.g., by application, to an isolated tissue or cell from a subject which is returned to the subject. The anti-GCC antibody molecule can be administered alone or in combination with a second agent. The treatment can be to cure, heal, alleviate, relieve, alter, remedy, ameliorate, palliate, improve or affect the disorder, the symptoms of the disorder or the predisposition toward the disorder, e.g., a cancer. While not wishing to be bound by theory, treating is believed to cause the inhibition, ablation, or killing of a cell in vitro or in vivo, or otherwise reducing capacity of a cell, e.g., an aberrant cell, to mediate a disorder, e.g., a disorder as described herein (e.g., a cancer).

As used herein, the term "subject" is intended to include mammals, primates, humans and non-human animals. For example, a subject can be a patient (e.g., a human patient or a veterinary patient), having a cancer, e.g., of gastrointestinal origin (e.g., colon cancer), a symptom of a cancer, e.g., of gastrointestinal origin (e.g., colon cancer), in which at least some of the cells express GCC, or a predisposition toward a cancer, e.g., of gastrointestinal origin (e.g., colon cancer), in which at least some of the cells express GCC. The term "non-human animals" of the invention includes all non-human vertebrates, e.g., non-human mammals and non-mammals, such as non-human primates, sheep, dog, cow, chickens, amphibians, reptiles, etc, unless otherwise noted. In an embodiment subject excludes one or more or all of a mouse, rat, rabbit or goat.

As used herein, an amount of an anti-GCC antibody molecule "effective" or "sufficient" to treat a disorder, or a "therapeutically effective amount" or "therapeutically sufficient amount" refers to an amount of the antibody molecule which is effective, upon single or multiple dose administration to a subject, in treating a cell, e.g., cancer cell (e.g., a GCC-expressing tumor cell), or in prolonging curing, alleviating, relieving or improving a subject with a disorder as described herein beyond that expected in the absence of such treatment. As used herein, "inhibiting the growth" of the tumor or cancer refers to slowing, interrupting, arresting or stopping its growth and/or metastases and does not necessarily indicate a total elimination of the tumor growth.

As used herein, "GCC," also known as "STAR", "GUC2C", "GUCY2C" or "ST receptor" protein refers to mammalian GCC, preferably human GCC protein. Typically, a naturally occurring allelic variant has an amino acid sequence at least 95%, 97% or 99% identical to the protein described in GenBank accession no.: NM.sub.—004963. GCC protein is characterized as a transmembrane cell surface receptor protein, and is believed to play a critical role in the maintenance of intestinal fluid, electrolyte homeostasis and cell proliferation.

Two hybridomas have been developed which secrete mouse monoclonal antibodies specific for the extracellular domain of GCC. These monoclonal antibodies, MS7 (IgG1k) and MS20 (IgG2ak), generated from BALB/c mice are capable of recognizing both human and mouse GCC. Production of mAb specific for the extracellular domain has not been previously reported. These antibodies are useful in a range of protein detection assays including western blot, ELISA, flow cytometry, and immunoimaging.

Monoclonal antibodies MS7 and MS20 and their derivatives (single chain variable fragments (scFv), diabodies, Fab fragments, humanized antibodies, immunotoxins, chimeric antigen receptors, etc.) may be used as a reagent for GCC protein detection in all in vitro techniques as well as for in vivo diagnostics (ex, imaging) and therapeutic targeting of GCC positive cells. These approaches may be employed for other cancers that may ectopically express GCC such as some esophageal and gastric cancers, as well has for normal healthy tissues which express GCC.

Anti-GCC antibodies, including both human and murine antibodies and fragments thereof are provided. The anti-GCC antibody molecules are useful as naked antibody molecules and as components of immunoconjugates. Accordingly, in another aspect, the invention features immunoconjugates comprising an anti-GCC antibody molecule and a therapeutic agent or label. The invention also features pharmaceutical compositions comprising the anti-GCC antibody molecules and immunoconjugates described herein. The invention also features methods of using the anti-GCC antibody molecules and immunoconjugates described herein for detection of GCC and of cells or tissues that express GCC; for diagnosis, prognosis, imaging, or staging of a GCC-mediated disease; for modulating an activity or function of a GCC protein; and for treatment of a GCC-mediated disease.

Isolated and/or recombinant nucleic acids encoding anti-GCC antibody molecule amino acid sequences are described, as well as vectors and host cells comprising such nucleic acids, and methods for producing anti-GCC antibody molecules.

Antibody molecules that bind to human guanylyl cyclase C are provided including compounds and compositions which comprise such antibodies and methods of making and using the same. Antibody molecule therapeutics directed to GCC can be used alone in unconjugated form to thereby inhibit the GCC-expressing cancerous cells. Anti-GCC antibody molecules of the invention can bind human GCC. In some embodiments, an anti-GCC antibody molecule of the invention can inhibit the binding of a ligand, e.g., guanylin or heat-stable enterotoxin to GCC. In other embodiments, an anti-GCC antibody molecule of the invention does not inhibit the binding of a ligand, e.g., guanylin or heat-stable enterotoxin to GCC.

Currently no technology exists to specifically and sensitively target the extracellular domain of GCC for both diagnostic and therapeutic uses. Moreover, these antibodies have the important characteristic of internalization upon GCC binding to cells. Therefore, these antibodies, as well as antibody conjugates are delivered to the inside of GCC-expressing cells.

```
MS7 heavy chain variable region Amino Acid
Sequence
                                   (SEQ. ID NO. 1)
EVMLVESGGG LVKPGGSLKL SCAASGFTFS TYAMSWVRQT

PEKRLEWVAT ITSGGSYTYY PDSVKGRFTI SRDNAKNILY

LQMSSLRSED TAMYYCTRLR QIGLRGFSDY WGQGTTLTVS

S

MS7 light chain variable region Amino Acid
Sequence
                                   (SEQ. ID. NO. 2)
DIDILMTQSP SSMYASLGER VTITCKASHD IKSYLSWYQQ

KPWRSPKTLI YYTTALADGV PSRFSGSGSG QDYSLTISSL

ESDDTATYYC LQHGESPYTF GGGTKLEIK

MS20 heavy chain variable region Amino Acid
Sequence
                                   (SEQ. ID. NO. 3)
EVQLEESGPE LVKPGASVKM SCKASGYTFT DYVISWVKQR

TGQGLEWIGV TYPGSGNTYY GERFKGKATL TVDKMSNTAY

MQLSSLTSED SAVYFCTRNY GSFYALDYWG QGTSVTVSS

MS20 light chain variable region Amino Acid
Sequence
                                   (SEQ. ID. NO. 4)
DIDILMTQSP ATLSVTPGDR VSLSCRASQS IRDYLHWYQH

RSHESPRLLI KYASQSISGI PSRFSGSGSG SDFTLTINSV

EPEDVGVYYC QNGHSFPTFG GGTKLEIK
```

Antibody molecules based upon MS7 and MS20 sequences can be used for GCC protein detection using a variety of immunoassays including western blot, ELISA, immunoimaging, and flow cytometry. Antibodies can be used to sort (enrich) GCC-expressing cells from samples containing rare GCC-expressing cells by magnetic, flow cytometric or similar techniques. For example, this can be used to enrich rare GCC-expressing metastatic colorectal cancer cells form blood for diagnostic, etc purposes. Antibodies can potentially be used to deliver imaging reagents in vivo in order to specifically locate GCC expressing tumors. Antibodies may be used to deliver imaging reagents to detect GCC-expressing tumors in vivo. Antibodies may be used to deliver toxins which can target and destroy GCC-expressing tumors in vivo. Antibodies may be used to deliver immunomodulatory agents to tumors to reduce adverse side effects and/or potentiate immune responses. For example, ant-CTLA4 antibody (ipilimumab), CD80/CD86, etc. scFv derived from these antibodies may be made and used to create chimeric antigen receptors (CAR) which can be inserted into effector immune cells for adoptive cell therapies targeting GCC-specific tumors. Antibodies may be used for intestinal delivery of small molecules, biologics, etc. Currently drug delivery systems are lacking for molecules with poor intestinal absorption and little or no bioavailability. Conjugating these to modified GCC-specific antibodies (for example IgA isotyped) may result in specific uptake by intestinal epithelium upon oral exposure resulting in systemic exposure. Modifications or derivatives of these antibodies which will make use of the antigen recognizing variable regions include, but are not limited to, single-chain variable fragments (scFv), diabodies, Fab fragments, humanized antibodies, and isotype modification which can potentially act as delivery/therapeutic agents. mAb's and derivatives may be used for delivery of imaging and cytotoxic agents to GCC+ tumors, as well as developing chimeric antigen receptors using mAb derived scFv for adoptive T cell therapy of GCC+ tumors.

In embodiments, the antibody molecules are not immunoconjugates, i.e., are "naked" and in embodiments cause a cellular reaction upon binding to GCC. In related embodiments, the cellular reaction is performed by the GCC-expressing cell to which the antibody binds. Such a cellular reaction can be signal transduction mediated by GCC, e.g., if the antibody molecule is an agonist of GCC (see, e.g., US Patent Application publication no. US20040258687. In other embodiments, the cellular reaction is performed by a second cell, e.g., an immune effector cell (e.g., a natural killer cell) which recognizes the antibody molecule bound to GCC on the first cell. In some embodiments, surveillance molecules, e.g., complement molecules, contact the GCC-bound antibody molecule prior to the cellular reaction. The cellular reactions in these embodiments can cause death of the GCC-expressing cell.

In further embodiments, antibody molecules which are immunoconjugates can both cause a cellular reaction upon binding to GCC and internalize to deliver an agent to the GCC-expressing cell to which it binds.

In some embodiments, an anti-GCC antibody molecule of the invention can block ligand binding to GCC.

In an embodiment, the anti-GCC antibody molecule fails to show substantial cross reaction with one or both of rat GCC and mouse GCC.

In an embodiment, the antibody molecule is not GCC: B10, GCC:4D7 or GCC:C8.

In another embodiment, an anti-GCC antibody molecule does not bind the kinase homology domain or the guanylyl cyclase domain of GCC.

The naturally occurring mammalian antibody structural unit is typified by a tetramer. Each tetramer is composed of two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains can be classified as kappa and lambda light chains. Heavy chains can be classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site. Preferred isotypes for the anti-GCC antibody molecules are IgG immunoglobulins, which can be classified into four subclasses, IgG1, IgG2, IgG3 and IgG4, having different gamma heavy chains. Most therapeutic antibodies are human, chimeric, or humanized antibodies of the IgG1 type. In a particular embodiment, the anti-GCC antibody molecule has the IgG1 isotype.

The variable regions of each heavy and light chain pair form the antigen binding site. Thus, an intact IgG antibody has two binding sites which are the same. However, bifunctional or bispecific antibodies are artificial hybrid constructs which have two different heavy/light chain pairs, resulting in two different binding sites.

The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989). As used herein, CDRs are referred to for each of the heavy (HCDR1, HCDR2, HCDR3) and light (LCDR1, LCDR2, LCDR3) chains.

An anti-GCC antibody molecule can comprise all, or an antigen binding subset of the CDRs, of one or both, the heavy and light chain, of one of the above-referenced human hybridoma, selected lymphocyte, or murine antibodies Amino acid sequences of human hybridoma, selected lymphocyte, and murine antibody portions, including variable regions and CDRs, can be found disclosed herein.

Thus, in an embodiment the antibody molecule includes one or both of: (a) one, two, three, or an antigen binding number of, light chain CDRs (LCDR1, LCDR2 and/or LCDR3) of one of the above-referenced human hybridoma, selected lymphocyte, or murine antibodies. In embodiments the CDR(s) may comprise an amino acid sequence of one or more or all of LCDR1-3 as follows: LCDR1, or modified LCDR1 wherein one to seven amino acids are conservatively substituted) LCDR2, or modified LCDR2 wherein one or two amino acids are conservatively substituted); or LCDR3, or modified LCDR3 wherein one or two amino acids are conservatively substituted; and (b) one, two, three, or an antigen binding number of, heavy chain CDRs (HCDR1, HCDR2 and/or HCDR3) of one of the above-referenced human hybridoma, selected lymphocyte, or murine antibodies. In embodiments the CDR(s) may comprise an amino acid sequence of one or more or all of HCDR1-3 as follows: HCDR1, or modified HCDR1 wherein one or two amino acids are conservatively substituted; HCDR2, or modified HCDR2 wherein one to four amino acids are conservatively substituted; or HCDR3, or modified HCDR3 wherein one or two amino acids are conservatively substituted.

Useful immunogens for production of anti-GCC antibodies include GCC e.g., human GCC-expressing cells (e.g., a tumor cell line, e.g., T84 cells, or fresh or frozen colon tumor cells, recombinant cells expressing GCC); membrane fractions of GCC-expressing cells (e.g., a colon tumor cell line, e.g., T84 cells, or fresh or frozen colonic tumor cells; isolated or purified GCC, e.g., human GCC protein (e.g., biochemically isolated GCC, e.g., isolated from gastrointestinal tumor cells or recombinant cells expressing GCC or a variant thereof), or a portion thereof (e.g., the extracellular domain of GCC, the kinase homology domain of GCC or the guanylyl cyclase catalytic domain of GCC or peptide corresponding to a portion thereof.

Immunogens can be fused to heterologous sequences to aid in biochemical manipulation, purification, immunization or antibody titer measurement. Such immunogens can comprise a portion of GCC, e.g., the extracellular domain, and a portion comprising a non-GCC polypeptide. Many options exist for constructing a fusion protein for ease of purification or immobilization onto a solid support, e.g., an affinity column or a microtiter plate or other suitable assay substrate/chip. For example, a fusion moiety can add a domain, e.g., glutathione-S-transferase/kinase (GST), which can bind glutathione; an Fc region of an immunoglobulin, which can bind to protein A or protein G; amino acid residues, e.g., two, three, four, five, preferably six histidine residues which can bind nickel or cobalt on an affinity column; an epitope tag, e.g., a portion of c-myc oncogene (myc-tag), a FLAG tag (U.S. Pat. No. 4,703,004), a hemagglutinin (HA) tag, a T7 gene 10 tag, a V5 tag, an HSV tag, or a VSV-G tag which can bind a tag-specific antibody; or a cofactor, e.g., biotin, which can bind streptavidin.

Immunogens which comprise the Fc portion of an immunoglobulin can hold the GCC, either in solution or attached to a cell, in a configuration which allows structural access to GCC epitopes by the host immune surveillance components for efficient antibody generation. Because immunoglobulin heavy chains comprising the Fc regions associate into dimers through interchain disulfide bonds, immunogens resulting from fusion with Fc regions are dimers. Valency of fusion proteins can reflect the type of immunoglobulin contributing an Fc region. For example, fusions with IgG proteins can be dimers, IgA fusions can make tetrameric immunogens, and IgM fusions can make decameric immunogens, the latter two is facilitated with co-transfection of the J chain. An exemplary immunoglobulin for an Fc fusion protein is IgG1. The portion used typically has the IgG1 hinge, CH2 and CH3 domains encoded by a single exon. Because this exon also has a portion of the CH1 region, which has a cysteine oriented to disulfide bond with a cysteine from the light chain, a useful modification is to mutate the CH1 cysteine, e.g., to a serine, to ensure there is no unpaired cysteine in the fusion protein. Such a mutation also increases flexibility of the hinge.

An Fc portion derived from a non-host species, e.g., human Ig Fc region, for fusing to an immunogen for immunization in a host species, e.g., mouse, rat, rabbit, goat, acts as an adjuvant. This adjuvant function can trigger specific antibodies against both Fc and GCC epitopes. Fc-reactive antibodies can be identified and discarded during screening. The Fc portion can have a wild type sequence or a sequence which is mutated to modify effector function. For example, a mutated constant region (variant) can be incorporated into a fusion protein to minimize binding to Fc receptors and/or ability to fix complement. (see e.g. Winter et al, GB 2,209,757 B; Morrison et al., WO 89/07142; Morgan et al., WO 94/29351).

To prepare a cell-expressed immunogen, the immunoglobulin portion can be structured to mimic an immunoglobulin portion of the B cell receptor. For example, the immunoglobulin Fc region can be further fused to a polypeptide comprising a transmembrane region from an immune receptor, such as Fc.gamma. receptors, Fc.alpha. receptors, Fc.alpha./.mu. receptor or Fc.epsilon. receptors. Proper orientation of such an Fc receptor cell-bound immunogen with adequate exposure on the cell surface may be improved if the cell expressing the immunogen fusion protein further comprises additional components of the antigen receptor complex, e.g., B cell IgM receptor or IgD receptor. Suitable components of the complex include immunoglobulin (Ig) sheath proteins, such as MB-1 and B29 (CD79A and CD79B; Hombach et al. Eur. J. Immunol. 20:2795-2799 (1990) for IgM receptor), which form a heterodimer. The Ig sheath proteins can be provided endogenously by the transfected cell, e.g., if transfecting a B cell lymphoma cell line; or by co-transfection of the immunogen with sheath proteins, e.g., in a separate vector or in the same vector. Preferred IgG sheath proteins for immunization in mouse are mouse CD79a and CD79b (GenBank Accession Nos. NM.sub.—007655 and NM.sub.—008339, respectively). A preferred cell-bound immunogen fusion protein (after maturation to cleave the signal peptide and translocation to the cell surface) is the TOK111 product, consisting of the TOK-107hIgG (hGCC-ECD/hIgG1 Fc) fused to the mouse IgG2a (e.g., GenPept Accession No. AAB59661) transmembrane and intracellular domains.

Useful epitopes, e.g., reference epitopes, from the GCC molecule, to which the anti-GCC antibody molecules, e.g., monoclonal antibodies, human antibodies or humanized antibodies, as described herein, can bind, can be found on the extracellular portion of GCC. Such GCC epitopes can bind antibody molecules on the surface of cells, e.g., on the cell exterior.

The anti-GCC antibody molecules can be polyclonal antibodies, monoclonal antibodies, monospecific antibodies, chimeric antibodies (See U.S. Pat. No. 6,020,153) or human or humanized antibodies or antibody fragments or derivatives thereof. Synthetic and genetically engineered variants (See U.S. Pat. No. 6,331,415) of any of the foregoing are also contemplated by the present invention. Monoclonal antibodies can be produced by a variety of techniques, including conventional murine monoclonal antibody methodology e.g., the standard somatic cell hybridization technique of Kohler and Milstein, Nature 256: 495 (1975). See generally, Harlow, E. and Lane, D. (1988) Antibodies: A Laboratory Manual, Cold Spring Harbor Laboratory Press, Cold Spring Harbor, N.Y. Generally, where a monoclonal antibody is desired, a hybridoma is produced by fusing a suitable cell from an immortal cell line with antibody-producing cells. Antibody-producing cells can be obtained from the peripheral blood or, preferably the spleen or lymph nodes, of humans, human-antibody transgenic animals or other suitable animals immunized with the antigen of interest. Cells that produce antibodies of human origin (e.g., a human antibody) can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., Hybridoma, 17:299-304 (1998); Zanella et al., J Immunol Methods, 156:205-215 (1992); Gustafsson et al., Hum Antibodies Hybridomas, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA (e.g., with immunogen, immobilized on the microtiter well) or by FACS on a cell expressing GCC or a portion thereof). For example, if the GCC-immunogen comprises a fusion moiety that is an affinity reagent, this moiety can allow the fusion protein comprising GCC or a portion thereof to be bound to a matrix, e.g., protein G-coated, streptavidin-coated, glutathione-derivatized or antibody-coated microtitre plates or assay chips, which are then combined with the immune serum or conditioned medium from a hybridoma or antibody-expressing recombinant cell, and the mixture incubated under conditions conducive to complex formation (e.g., at physiological conditions for salt and pH). Following incubation, the microtitre plate wells or chip cells are washed to remove any unbound components and binding by anti-GCC antibody is measured.

In embodiments, for therapeutic applications, the antibodies of the present invention are human or humanized antibodies. The advantage of human or humanized antibodies is that they potentially decrease or eliminate the immunogenicity of the antibody in a host recipient, thereby permitting an increase in the bioavailability and a reduction in the possibility of adverse immune reaction, thus potentially enabling multiple antibody administrations.

Modified antibodies include humanized, chimeric or CDR-grafted antibodies. Human anti-mouse antibody (HAMA) responses have led to development of chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. The presence of such murine or rat derived proteins can lead to the rapid clearance of the antibodies or can lead to the generation of an immune response against the antibody by a patient. In order to avoid the utilization of murine or rat derived antibodies, humanized antibodies where sequences are introduced to an antibody sequence to make it closer to human antibody sequence, or fully human antibodies generated by the introduction of human antibody function into a rodent have been developed so that the rodent would produce antibodies having fully human sequences. Human antibodies avoid certain of the problems associated with antibodies that possess murine, rabbit, or rat variable and/or constant regions.

Fully human antibody molecules can minimize the immunogenic and allergic responses intrinsic to mouse or mouse-derivatized mAbs and thus to increase the efficacy and safety of the administered antibodies. The use of fully human antibody molecules can provide a substantial advantage in the treatment of chronic and recurring human diseases, such as inflammation, autoimmunity, and cancer, which require repeated antibody administrations. Also, human antibody molecules can be produced using genetically engineered strains of animals in which the antibody gene expression of the animal is suppressed and functionally replaced with human antibody molecule gene expression.

Methods for making human antibodies are known in the art. One method for making human antibodies employs the use of transgenic animals, such as a transgenic mouse. These transgenic animals contain a substantial portion of the human antibody producing genome, e.g., a human immunoglobulin locus that can undergo functional rearrangement, inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference. Other transgenic human antibody-producing mice include HUMAB-MOUSE™, KIRIN TC MOUSE™ transchromosome mice, KM-MOUSE™ (MEDAREX, Princeton, N.J.).

Using the human antibody transgenic animal technology, e.g., XENOMOUSE™ technology, human antibodies can be obtained by immunizing a XENOMOUSE™ mouse (Abgenix, Fremont, Calif.) with an antigen of interest. The lymphatic cells (such as B-cells) are recovered (e.g., isolated from spleen tissue) from the mice that express antibodies. These recovered cells can be fused with a myeloid-type cell line to prepare immortal hybridoma cell lines, using standard methodology. These hybridoma cell lines can be screened and selected to identify hybridoma cell lines that produce antibodies specific to the antigen of interest.

Human-antibody transgenic animals provide a source of nucleic acids that can be enriched in nucleic acids that encode antibodies having desired properties, such as specificity and affinity. For example, nucleic acids encoding antibodies or antibody variable regions can be isolated from human-antibody transgenic mice that have been immunized with a GCC protein or variant or portion thereof. The isolated nucleic acids or portions thereof (e.g., portions encoding variable regions, CDRs, framework regions) can be expressed using any suitable method (e.g., phage display) to produce a library of antibodies or antigen-binding fragments of antibodies (e.g., single chain antigen-binding fragments, double chain antigen-binding fragments) that is enriched for antibodies or antigen-binding fragments that bind a GCC protein. Such a library can exhibit enhanced diversity (e.g., combinatorial diversity through pairing of heavy chain variable regions and light chain variable regions) relative to the repertoire of antibodies produced in the immunized human-antibody transgenic animal. The library can be screened using any suitable assay (e.g., a GCC protein binding assay) to identify antibodies or antigen-binding fragments having desired properties (e.g., specificity, affinity). The nucleic acids encoding antibody or antigen-binding fragments having desired properties can be recovered using any suitable method. (See, e.g., U.S. Pat. No. 5,871,907 (Winter et al.) and U.S. Pat. No. 6,057,098 (Buechler et al.).)

Alternatively, the antibodies can be expressed in cell lines other than hybridoma cell lines. More specifically, sequences encoding particular antibodies can be cloned from cells producing the antibodies and used for transformation of a suitable mammalian host cell. In a preferred method, spleen and/or lymph node lymphocytes from immunized mice are isolated from the mice and plated in plaque assays as described previously in Babcook et al., Proc Natl Acad Sci USA. 93: 7843-8 (1996), which is incorporated herein by reference. Briefly, cells are plated in agar with sheep red blood cells, coated with GCC antigen and cells secreting mAb against the GCC antigen would fix complement and lyse the red blood cells immediately surrounding the mAb producing cells. Cells within the cleared plaques are lifted for sequencing of the immunoglobulin sequences and subcloning into expression vectors. Supernatants from transiently transfected cells containing GCC specific mAb are subsequently screened by ELISA and for binding to cells by flow cytometry. The variable sequences, or a portion thereof of the produced human antibodies comprising CDRs which bind particular epitopes may be utilized for production of modified antibodies. For example, the variable regions of the produced antibodies may be spliced into an expression cassette for ease of transfer of constructs, increased expression of constructs, and/or incorporation of constructs into vectors capable of expression of full length antibodies, see, e.g., US20060147445. In a particular embodiment, the expression cassette comprises the heavy chain constant region of the IgG1 isotype.

The Selected Lymphocyte Antibody Method (SLAM, see U.S. Pat. No. 5,627,052, Babcook et al. Proc. Natl. Acad. Sci. U.S.A. 93:7843-7848 (1996)) can also be used to identify cells which can provide the antibody of interest. In SLAM, B-cells are cultured directly, thus bypassing hybridoma technology, which typically captures only small percentage of the antibodies originally generated by a mouse. Using microplate-based assays, the B-cells are rapidly assayed over a period of several days. Typically, thousands of antigen-reactive cell-clones are identified, representing thousands of individual antigen-specific, e.g., GCC-specific, monoclonal antibodies. The number of different antigen-reactive monoclonal antibodies identified in a single experiment is typically increased many-fold. After applying additional rapid microplate-based assays to measure and rank antibodies by affinity and function, individual B-cell clones producing extremely high quality antibodies can be selected. In addition, by bypassing the hybridoma generation step, production can move rapidly into a recombinant manufacturing cell line. Individual B cells selected using the technology are isolated and the antibody genes can be directly introduced into a manufacturing cell line. The resulting cell line then can be developed for clinical trial testing over essentially the same timeline as that required for hybridoma cell line development.

As discussed above, there are advantages to producing antibodies with reduced immunogenicity. This can be accomplished in connection with techniques of humanization and display techniques using appropriate libraries. It will be appreciated that murine antibodies or antibodies from other species can be humanized or primatized using techniques known in the art. See e.g., Winter and Harris Immunol Today 14:43-46 (1993) and Wright et al. Crit. Reviews in Immunol. 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. Proc Natl Acad Sci USA. 84:3439 (1987) and J. Immunol. 139:3521 (1987)). mRNA is isolated from a hybridoma or other cell producing the antibody and used to produce cDNA: The cDNA of interest may be amplified by the polymerase chain reaction using specific primers (U.S. Pat. Nos. 4,683,195 and 4,683,202).

Alternatively, phage display technology (see, e.g., McCafferty et al, Nature, 348:552-553 (1990)) can be used to produce human antibodies and antibody fragments in vitro, from immunoglobulin variable (V) domain genes, e.g., from repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson and Chiswell, Current Opinion in Structural Biology, 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al, EMBO J., 12:725-734 (1993). See, also, U.S. Pat. Nos. 5,565,332 and 5,573,905. Display libraries can contain antibodies or antigen-binding fragments of antibodies that contain artificial amino acid sequences. For example, the library can contain Fab fragments which contain artificial CDRs (e.g., random amino acid sequences) and human framework regions. (See, for example, U.S. Pat. No. 6,300,064 (Knappik, et al.).)

Human antibodies may also be generated by in vitro activated B cells (see U.S. Pat. Nos. 5,567,610 and 5,229, 275).

The sequences of human constant region genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Isotypes can be IgG1, IgG2, IgG3 or IgG4. In particular embodiments, antibody molecules of the invention are IgG1 and IgG2. Either of the human light chain constant regions, kappa or lambda, may be used. The chimeric, humanized antibody is then expressed by conventional methods.

In some embodiments, an anti-GCC antibody molecule of the invention can draw antibody-dependent cellular cytotoxicity (ADCC) to a cell expressing GCC, e.g., a tumor cell. Antibodies with the IgG1 and IgG3 isotypes are useful for eliciting effector function in an antibody-dependent cytotoxic capacity, due to their ability to bind the Fc receptor. Antibodies with the IgG2 and IgG4 isotypes are useful to minimize an ADCC response because of their low ability to bind the Fc receptor. In related embodiments substitutions in the Fc region or changes in the glycosylation composition of an antibody, e.g., by growth in a modified eukaryotic cell line, can be made to enhance the ability of Fc receptors to recognize, bind, and/or mediate cytotoxicity of cells to which anti-GCC antibodies bind (see, e.g., U.S. Pat. Nos. 7,317,091, 5,624,821 and publications including WO 00/42072, Shields, et al. J. Biol. Chem. 276:6591-6604 (2001), Lazar et al. Proc. Natl. Acad. Sci. U.S.A. 103:4005-4010 (2006), Satoh et al. Expert Opin Biol. Ther. 6:1161-1173 (2006)). In certain embodiments, the antibody or antigen-binding fragment (e.g., antibody of human origin, human antibody) can include amino acid substitutions or replacements that alter or tailor function (e.g., effector function). For example, a constant region of human origin (e.g., .gamma.1 constant region, .gamma.2 constant region) can be designed to reduce complement activation and/or Fc receptor binding. (See, for example, U.S. Pat. No. 5,648,260 (Winter et al.), U.S. Pat. No. 5,624,821 (Winter et al.) and U.S. Pat. No. 5,834,597 (Tso et al.), the entire teachings of which are incorporated herein by reference.) Preferably, the amino acid sequence of a constant region of human origin that contains such amino acid substitutions or replacements is at least about 95% identical over the full length to the amino acid sequence of the unaltered constant region of human origin, more preferably at least about 99% identical over the full length to the amino acid sequence of the unaltered constant region of human origin.

In still another embodiment, effector functions can also be altered by modulating the glycosylation pattern of the antibody. By altering is meant deleting one or more carbohydrate moieties found in the antibody, and/or adding one or more glycosylation sites that are not present in the antibody. For example, antibodies with enhanced ADCC activities with a mature carbohydrate structure that lacks fucose attached to an Fc region of the antibody are described in U.S. Patent Application Publication No. 2003/0157108 (Presta). See also U.S. Patent Application Publication No. 2004/0093621 (Kyowa Hakko Kogyo Co., Ltd). Glycofi has also developed yeast cell lines capable of producing specific glycoforms of antibodies.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which are engineered to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Humanized antibodies can be made using a CDR-grafted approach. Techniques of generation of such humanized antibodies are known in the art. Generally, humanized antibodies are produced by obtaining nucleic acid sequences that encode the variable heavy and variable light sequences of an antibody that binds to GCC, identifying the complementary determining region or "CDR" in the variable heavy and variable light sequences and grafting the CDR nucleic acid sequences on to human framework nucleic acid sequences. (See, for example, U.S. Pat. Nos. 4,816,567 and 5,225,539). The location of the CDRs and framework residues can be determined (see, Kabat, E. A., et al. (1991) Sequences of Proteins of Immunological Interest, Fifth Edition, U.S. Department of Health and Human Services, NIH Publication No. 91-3242, and Chothia, C. et al. J. Mol. Biol. 196:901-917 (1987)). Anti-GCC antibody molecules described herein have the CDR amino acid sequences and nucleic acid sequences encoding CDRs listed in Tables 5 and 6. In some embodiments sequences from Tables 5 and 6 can be incorporated into molecules which recognize GCC for use in the therapeutic or diagnostic methods described herein. The human framework that is selected is one that is suitable for in vivo administration, meaning that it does not exhibit immunogenicity. For example, such a determination can be made by prior experience with in vivo usage of such antibodies and studies of amino acid similarities. A suitable framework region can be selected from an antibody of human origin having at least about 65% amino acid sequence identity, and preferably at least about 70%, 80%, 90% or 95% amino acid sequence identity over the length of the framework region within the amino acid sequence of the equivalent portion (e.g., framework region) of the donor antibody, e.g., an anti-GCC antibody molecule (e.g., 3G1). Amino acid sequence identity can be determined using a suitable amino acid sequence alignment algorithm, such as CLUSTAL W, using the default parameters. (Thompson J. D. et al., Nucleic Acids Res. 22:4673-4680 (1994).)

Once the CDRs and FRs of the cloned antibody that are to be humanized are identified, the amino acid sequences encoding the CDRs are identified and the corresponding nucleic acid sequences grafted on to selected human FRs. This can be done using known primers and linkers, the selection of which are known in the art. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen. After the CDRs are grafted onto selected human FRs, the resulting "humanized" variable heavy and variable light sequences are expressed to produce a humanized Fv or humanized antibody that binds to GCC. Preferably, the CDR-grafted (e.g., humanized) antibody binds a GCC protein with an affinity similar to, substantially the same as, or better than that of the donor antibody. Typically, the humanized variable heavy and light sequences are expressed as a fusion protein with human constant domain sequences so an intact antibody that binds to GCC is obtained. However, a humanized Fv antibody can be produced that does not contain the constant sequences.

Also within the scope of the invention are humanized antibodies in which specific amino acids have been substituted, deleted or added. In particular, humanized antibodies can have amino acid substitutions in the framework region, such as to improve binding to the antigen. For example, a selected, small number of acceptor framework residues of the humanized immunoglobulin chain can be replaced by the corresponding donor amino acids. Locations of the substitutions include amino acid residues adjacent to the CDR, or which are capable of interacting with a CDR (see e.g., U.S. Pat. No. 5,585,089 or 5,859,205). The acceptor framework can be a mature human antibody framework sequence or a consensus sequence. As used herein, the term "consensus sequence" refers to the sequence found most frequently, or devised from the most common residues at each position in a sequence in a region among related family members. A number of human antibody consensus sequences are available, including consensus sequences for the different subgroups of human variable regions (see, Kabat, E. A., et al., Sequences of Proteins of Immunological Interest, Fifth Edition, U.S. Department of Health and Human Services, U.S. Government Printing Office (1991)). The Kabat database and its applications are freely available on line, e.g. via IgBLAST at the National Center for Biotechnology Information, Bethesda, Md. (also see, Johnson, G. and Wu, T. T., Nucleic Acids Research 29:205-206 (2001)).

Other techniques for humanizing antibodies are described in Padlan et al. EP 519596 A1, published on Dec. 23, 1992.

The anti-GCC antibody molecule includes other humanized antibodies which may also be modified by specific deletion of human T cell epitopes or "deimmunization" by the methods disclosed in PCT Publication Nos. WO 98/52976 and WO 00/34317, the contents of which are incorporated herein by reference. Briefly, the murine heavy and light chain variable regions of an anti-GCC antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the murine VH and VL sequences, as described in PCT Publication Nos. WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made, often but not exclusively, an amino acid common at this position in human germline antibody sequences may be used. Human germline sequences are disclosed in Tomlinson, I. A. et al., J. Mol. Biol. 227:776-798 (1992); Cook, G. P. et al., Immunol. Today Vol. 16 (5): 237-242 (1995); Chothia, D. et al., J. Mol. Bio. 227:799-817 (1992). The V BASE directory provides a comprehensive directory of human immunoglobulin variable region sequences (compiled by Tomlinson, I. A. et al. MRC Centre for Protein Engineering, Cambridge, UK). After the deimmunized VH and VL of an anti-GCC antibody are constructed by mutagenesis of the murine VH and VL genes, the mutagenized variable sequence can, optionally, be fused to a human constant region, e.g., human IgG1 or kappa-constant regions.

In other embodiments, reduction of an immunogenic response by a CDR-grafted antibody can be achieved by changes, e.g., deletions, substitutions, of amino acid residues in CDRs (Kashmiri et al. Methods 36:25-34 (2005), U.S. Pat. No. 6,818,749, Tan et al. J. Immunol. 169:1119-1125 (2006)). For example, residues at positions involved in contact with the antigen preferably would not be changed. Typically, such residues, the SDRs, are in positions which display high levels of variability among antibodies. Consensus sequences derived, e.g., by the Clustal method (Higgins D. G. et al., Meth. Enzymol. 266:383-402 (1996)), from anti-GCC antibody molecules, e.g., from antibodies described herein, aid in identifying SDRs. In the human anti-GCC antibody molecules described herein, the SDRs are the following, at least the first residue or in some embodiments, the first four residues of heavy chain CDR1; at least the N-terminal portion, e.g., the first seven, ten or 13 residues of heavy chain CDR2; nearly all of heavy chain CDR3; the C-terminal portion, e.g., after residue six, eight, or nine of light chain CDR1; about the first, middle and/or last residue of light chain CDR2; and most of light chain CDR3, or at least after residue two or three. Accordingly, to maintain binding to GCC protein after humanization or modification of an anti-GCC antibody molecule, such SDR residues in CDRs of the anti-GCC antibody molecules are less amenable to changes, e.g., from murine residues to human consensus residues than are residues in other residues of the CDRs or the framework regions. Conversely, it can be beneficial to change residues in non-human, e.g., murine CDRs to residues identified as consensus in human CDRs, e.g., CDRs of anti-GCC antibody molecules described herein. For example, a serine can represent a human residue for the C-terminus of heavy chain CDR1, and/or a tyrosine can represent a human residue for the second and/or third residues of heavy chain CDR1; heavy chain CDR2 can end in S-(L/V)-K-(S/G) to represent a human CDR; to represent a human CDR3, there can be a glycine after four to six residues and/or an aspartate six to nine residues in heavy chain CDR3; light chain CDR1 can begin with (K/R)-(A/S)-SQS-(V/L)-(S/L) to represent a human CDR; light chain CDR2 can have a serine in the third residue and/or an arginine in the fifth residue represent a human CDR; and/or light chain CDR3 can have a glutamine in the second residue and/or a tyrosine or serine in the third residue represent a human CDR.

Anti-GCC antibodies that are not intact antibodies are also useful in this invention. Such antibodies may be derived from any of the antibodies described above. Useful antibody molecules of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; (vii) a single domain functional heavy chain antibody, which consists of a VHH domain (known as a nanobody) see e.g., Cortez-Retamozo, et al., Cancer Res. 64: 2853-2857 (2004), and references cited therein; and (vii) an isolated CDR, e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1988); and Huston et al. Proc. Natl. Acad. Sci. USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

In embodiments, some or all of the CDRs sequences, of one or both the heavy and light chain, can be used in another antibody molecule, e.g., in a CDR-grafted, humanized, or chimeric antibody molecule.

Embodiments include an antibody molecule that comprises sufficient CDRs, e.g., all six CDRs from one of the above-referenced human hybridoma, selected lymphocyte, or murine antibodies to allow binding to cell surface GCC.

In an embodiment the CDRs, e.g., all of the HCDRs, or all of the LCDRs, or all six, are embedded in human or human derived framework region(s). Examples of human framework regions include human germline framework sequences, human germline sequences that have been affinity matured (either in vivo or in vitro), or synthetic human sequences, e.g., consensus sequences. In an embodiment the heavy chain framework is an IgG1 or IgG2 framework. In an embodiment the light chain framework is a kappa framework.

In an embodiment the anti-GCC antibody molecule, e.g., a CDR-grafted or humanized antibody molecule, comprises sufficient CDRs, e.g., all six CDRs from one of the antibodies described herein to allow binding to GCC.

Antibody fragments for in vivo therapeutic or diagnostic use can benefit from modifications which improve their serum half lives. Suitable organic moieties intended to increase the in vivo serum half-life of the antibody can include one, two or more linear or branched moiety selected from a hydrophilic polymeric group (e.g., a linear or a branched polymer (e.g., a polyalkane glycol such as polyethylene glycol, monomethoxy-polyethylene glycol and the like), a carbohydrate (e.g., a dextran, a cellulose, a polysaccharide and the like), a polymer of a hydrophilic amino acid (e.g., polylysine, polyaspartate and the like), a polyalkane oxide and polyvinyl pyrrolidone), a fatty acid group (e.g., a mono-carboxylic acid or a di-carboxylic acid), a fatty acid ester group, a lipid group (e.g., diacylglycerol group, sphingolipid group (e.g., ceramidyl)) or a phospholipid group (e.g., phosphatidyl ethanolamine group). Preferably, the organic moiety is bound to a predetermined site where the organic moiety does not impair the function (e.g., decrease the antigen binding affinity) of the resulting immunoconjugate compared to the non-conjugated antibody moiety. The organic moiety can have a molecular weight of about 500 Da to about 50,000 Da, preferably about 2000, 5000, 10,000 or 20,000 Da. Examples and methods for modifying polypeptides, e.g., antibodies, with organic moieties can be found, for example, in U.S. Pat. Nos. 4,179,337 and 5,612,460, PCT Publication Nos. WO 95/06058 and WO 00/26256, and U.S. Patent Application Publication No. 20030026805.

In an embodiment the light chain amino acid sequence of (a) can differ from one of the reference amino acid sequence(s) referred to in (a)(i-ii) by as many as 1, 2, 3, 4, 5, 10, or 15 residues. In embodiments the differences are conservative substitutions. In embodiments, the differences are in the framework regions. In an embodiment the heavy chain amino acid sequence of (b) can differ from one of the reference amino acid sequence(s) referred to in (b)(i-ii) by as many as 1, 2, 3, 4, 5, 10, or 15 residues. In embodiments the differences are conservative substitutions. In embodiments the differences are in the framework regions.

In an embodiment the anti-GCC antibody molecule comprises one or both of: a) a light chain variable region, or an antigen binding fragment thereof, having at least 85, 90, 95, 97 or 99% homology with the light chain variable region of an anti-GCC antibody molecule of the invention; and (b) a heavy chain variable region, or an antigen binding fragment thereof, having at least 85, 90, 95, 97 or 99% homology with the heavy chain variable region of an anti-GCC antibody molecule of the invention.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Polyadenylation and transcription termination occur at native chromosomal sites downstream of the coding regions. The resulting chimeric antibody may be joined to any strong promoter. Examples of suitable vectors that can be used include those that are suitable for mammalian hosts and based on viral replication systems, such as simian virus 40 (SV40), Rous sarcoma virus (RSV), adenovirus 2, bovine papilloma virus (BPV), papovavirus BK mutant (BKV), or mouse and human cytomegalovirus (CMV), and moloney murine leukemia virus (MMLV), native Ig promoters, etc. A variety of suitable vectors are known in the art, including vectors which are maintained in single copy or multiple copies, or which become integrated into the host cell chromosome, e.g., via LTRs, or via artificial chromosomes engineered with multiple integration sites (Lindenbaum et al. Nucleic Acids Res. 32:e172 (2004), Kennard et al. Biotechnol. Bioeng. Online May 20, 2009). Additional examples of suitable vectors are listed in a later section.

Thus, the invention provides an expression vector comprising a nucleic acid encoding an antibody, antigen-binding fragment of an antibody (e.g., a human, humanized, chimeric antibody or antigen-binding fragment of any of the foregoing), antibody chain (e.g., heavy chain, light chain) or antigen-binding portion of an antibody chain that binds a GCC protein.

Expression in eukaryotic host cells is useful because such cells are more likely than prokaryotic cells to assemble and secrete a properly folded and immunologically active antibody. However, any antibody produced that is inactive due to improper folding may be renaturable according to known methods (Kim and Baldwin, "Specific Intermediates in the Folding Reactions of Small Proteins and the Mechanism of Protein Folding", Ann. Rev. Biochem. 51, pp. 459-89 (1982)). It is possible that the host cells will produce portions of intact antibodies, such as light chain dimers or heavy chain dimers, which also are antibody homologs according to the present invention.

Further, as described elsewhere herein, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are known in the art. Winter and Harris Immunol Today 14:43-46 (1993) and Wright et al. Crit. Reviews in Immunol. 12125-168 (1992), Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. Proc Natl Acad Sci USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743. If display technologies are utilized to produce antibodies that are not human, such antibodies can be humanized as described above.

It will be appreciated that antibodies that are generated need not initially possess a particular desired isotype but, rather, the antibody as generated can possess any isotype. The isotype of the antibody can be switched thereafter, e.g., to IgG1 or IgG3 to elicit an ADCC response when the antibody binds GCC on a cell, using conventional techniques that are known in the art. Such techniques include the use of direct recombinant techniques (see e.g., U.S. Pat. No. 4,816,397), cell-cell fusion techniques (see e.g., U.S. Pat. No. 5,916,771), among others. In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

In certain embodiments, the GCC antibody molecule is a human anti-GCC IgG1 antibody. Since such antibodies possess desired binding to the GCC molecule, any one of such antibodies can be readily isotype-switched to generate a human IgG4 isotype, for example, while still possessing the same variable region (which defines the antibody's specificity and affinity, to a certain extent). Accordingly, as antibody candidates are generated that meet desired "structural" attributes as discussed above, they can generally be provided with at least certain additional "functional" attributes that are desired through isotype switching.

In an embodiment the variable region or antigen binding fragment thereof can be coupled to a constant region (or fragment thereof) other than the constant region it was generated with, e.g., a constant region (or fragment thereof) from another antibody or to a synthetic constant region (or fragment thereof). In embodiments the constant region is an IgG1 or IgG2 constant region (or fragment thereof). Sequence changes can be made in the variable or constant regions to modify effector activity of the antibody molecule.

The antibodies that are produced and characterized herein with respect to GCC provide for the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunoconjugates, and radiolabeled therapeutics, generation of peptide therapeutics, particularly intrabodies, and small molecules. Furthermore, as discussed above, the effector function of the antibodies of the invention may be changed by isotype switching to an IgG1, IgG2, IgG3, IgG4, IgD, IgA1, IgA2, IgE, or IgM for various therapeutic uses.

In connection with bispecific antibodies, bispecific antibodies can be generated that comprise (i) two antibodies, one with a specificity to GCC and another to a second molecule that are conjugated together, (ii) a single antibody that has one chain specific to GCC and a second chain specific to a second molecule, or (iii) a single chain antibody that has specificity to GCC and the other molecule. Such bispecific antibodies can be generated using techniques that are known. For example, bispecific antibodies may be produced by crosslinking two or more antibodies (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. See also, e.g., Fanger et al. Immunomethods 4:72-81 (1994) and Winter and Harris Immunol Today 14:43-46 (1993) and Wright et al. Crit. Reviews in Immunol. 12125-168 (1992) and in connection with (iii) see e.g., Traunecker et al. Int. J. Cancer (Suppl.) 7:51-52 (1992). Songsivilai & Lachmann Clin. Exp. Immunol. 79: 315-321 (1990), Kostelny et al. J. Immunol. 148:1547-1553 (1992).

In addition, "Kappabodies" (Ill. et al. "Design and construction of a hybrid immunoglobulin domain with properties of both heavy and light chain variable regions" Protein Eng 10:949-57 (1997)), "Minibodies" (Martin et al. EMBO J. 13:5303-9 (1994), U.S. Pat. No. 5,837,821), "Diabodies" (Holliger et al. Proc Natl Acad Sci USA 90:6444-6448 (1993)), or "Janusins" (Traunecker et al. EMBO J. 10:3655-3659 (1991) and Traunecker et al. Int J Cancer Suppl 7:51-52 (1992)) may also be prepared.

In another embodiment, the present invention relates to polynucleotide and polypeptide sequences that encode for or represent the antibody molecules described herein. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence which coding sequence, as a result of the redundancy or degeneracy of the genetic code, encodes the same polypeptide as the DNA provided herein.

The present invention also includes variant polynucleotides containing modifications such as polynucleotide deletions, substitutions or additions, and any polypeptide modification resulting from the variant polynucleotide sequence. A polynucleotide of the present invention may also have a coding sequence that is a variant of the coding sequence provided herein. For example, a variant polynucleotide can have at least 50%, 60%, 70%, 75%, 80%, 85%, 90%, 95% or 97% identity with an anti-GCC antibody molecule.

The present invention further relates to polypeptides that represent the antibodies of the present invention as well as fragments, analogs and derivatives of such polypeptides. The polypeptides of the present invention may be recombinant polypeptides, naturally produced polypeptides or synthetic polypeptides. The fragment, derivative or analogs of the polypeptides of the present invention may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence that is employed for purification of the polypeptide or a proprotein sequence. Such fragments, derivatives and analogs are within the scope of the present invention. In various aspects, the polypeptides of the invention may be partially purified, or purified product.

A polypeptide of the present invention can have an amino acid sequence that is identical to that of the antibodies described herein or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine; replacement of lysine with arginine or histidine. In contrast, variations may include nonconservative changes, e.g., replacement of a glycine with a tryptophan. Similar minor variations may also include amino acid deletions or insertions or both. Guidance in determining which and how many amino acid residues may be substituted, inserted, or deleted without changing biological or immunological activity may be found using computer programs known in the art, for example DNASTAR software (DNASTAR, Inc., Madison, Wis.).

In another aspect, the invention features, isolated and/or recombinant nucleic acids encoding anti-GCC antibody molecules. In embodiments, the nucleic acids encode one or more of an antibody molecule, a heavy chain, a light chain, a light chain variable region, a heavy chain variable region, portions of the heavy chains and light chains of the antibody molecules described herein (e.g., a light chain variable region fragment which when paired with a full length heavy chain variable region is antigen binding, or a heavy chain variable region fragment which when paired with a full length light chain variable region is antigen binding), and CDRs.

In embodiments provided, polynucleotides encode at least one heavy chain variable region or at least one light chain variable region of the antibodies of the present invention. In embodiments provided, polypeptides can encode at least one heavy chain variable region and one light chain variable region of the antibodies of the present invention.

In an embodiment selected stringency conditions are high stringency or very high stringency conditions, e.g., as those conditions are described herein.

The present invention also provides vectors that include the polynucleotides of the present invention, host cells which are genetically engineered with vectors of the present invention and the production of the antibodies of the present invention by recombinant techniques.

The appropriate DNA sequence may be inserted into the vector by a variety of procedures. In general, the DNA sequence is inserted into appropriate restriction endonuclease sites by procedures known in the art. The polynucleotide sequence in the expression vector is operatively linked to an appropriate expression control sequence (i.e. promoter) to direct mRNA synthesis. Examples of such promoters include, but are not limited to, the Rous sarcoma virus LTR or the early or late SV40 promoter, the *E. coli* lac or trp, the phage lambda P.sub.L promoter and other promoters known to control expression of genes in prokaryotic (e.g., tac, T3, T7 promoters for *E. coli*) or eukaryotic (e.g., cytomegalovirus promoter, adenovirus late promoter, EF-1a promoter) cells or their viruses. The expression vector also contains a ribosome binding site for translation initiation and a transcription terminator. The vector may also include appropriate sequences for amplifying expression. For example, the vector can contain enhancers, which are transcription-stimulating DNA sequences of viral origin, such as those derived form simian virus such as SV40, polyoma virus, cytomegalovirus, bovine papilloma virus or Moloney sarcoma virus, or genomic, origin. The vector preferably also contains an origin of replication. The vector can be constructed to contain an exogenous origin of replication or, such an origin of replication can be derived from SV40 or another viral source, or by the host cell chromosomal replication mechanism.

In addition, the vectors optionally contain a marker gene for selection of transfected host cells such as dihydrofolate reductase marker genes to permit selection with methotrexate in a variety of hosts, or antibiotics, such as .beta.-lactamase gene (ampicillin resistance), Tet gene (for tetracycline resistance) used in prokaryotic cells or neomycin, GA418 (geneticin, a neomycin-derivative) gpt (mycophenolic acid), ampicillin, or hygromycin resistance genes, or genes which complement a genetic lesion of the host cells such as the absence of thymidine kinase, hypoxanthine phosphoribosyl transferase, dihydrofolate reductase, etc.

Genes encoding the gene product of auxotrophic markers of the host (e.g., LEU2, URA3, HIS3) are often used as selectable markers in yeast.

In order to obtain the antibodies of the present invention, one or more polynucleotide sequences that encode for the light and heavy chain variable regions and light and heavy chain constant regions of the antibodies of the present invention should be incorporated into a vector. Polynucleotide sequences encoding the light and heavy chains of the antibodies of the present invention can be incorporated into one or multiple vectors and then incorporated into the host cells.

Suitable expression vectors for expression in mammalian cells include, for example, pCDM8, pcDNA1.1/amp, pcDNA3.1, pRc/RSV, pEF-1 (Invitrogen Life Technologies, Carlsbad, Calif.), pCMV-SCRIPT, pFB, pSG5, pXT1 (Stratagene, La Jolla, Calif.), pCDEF3 (Goldman, L. A., et al., Biotechniques, 21:1013-1015 (1996)), pSVSPORT (GIBCO division of Invitrogen Life Technologies, Carlsbad, Calif.), pEF-Bos (Mizushima, S., et al., Nucleic Acids Res., 18:5322 (1990)), Bicistronic GPEX® Retrovector (Gala Biotech, Middleton, Wis.) and the like. Expression vectors which are suitable for use in various expression hosts, such as prokaryotic cells (E. coli), insect cells (Drosophila Schnieder S2 cells, Sf9) and yeast (P. methanolica, P. pastoris, S. cerevisiae) are also available.

As will be appreciated, antibodies in accordance with the present invention can be expressed in cell lines other than hybridoma cell lines. Sequences encoding the cDNAs or genomic clones for the particular antibodies can be used for a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, for introducing heterologous polynucleotides into mammalian cells, e.g., dextran-mediated transfection, calcium phosphate precipitation, polybrene mediated transfection, protoplast fusion, electroporation, encapsulation of the polynucleotide(s) into liposomes and direct microinjection of the DNA molecule. The transformation procedure used depends upon the host to be transformed. Methods for introduction of heterologous polynucleotides into mammalian cells are known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

In another aspect, the invention features, a host cell comprising a nucleic acid described herein. In embodiments the cell expresses an antibody molecule, or component thereof, described herein. Still further embodiment provides a method of producing an antibody molecule, e.g., an anti-GCC antibody molecule described herein, e.g. a human or humanized antibody molecule comprising maintaining the host cell under conditions appropriate for expression, whereby immunoglobulin chain(s) are expressed and an antibody molecule is produced. An additional embodiment provides a host cell comprising any of the foregoing expression vectors encoding heavy and light chain antibody sequences. The host cell can be a eukaryotic cell, e.g., a mammalian cell, an insect cell, a yeast cell, or a prokaryotic cell, e.g., E. coli. For example, the mammalian cell can be a cultured cell or a cell line. Additionally cells include oocyte cells, and cells from a transgenic animal, e.g., mammary epithelial cell. For example, nucleic acids encoding an antibody molecule described herein can be expressed in a transgenic nonhuman animal.

Mammalian cell lines available as hosts for expression are known in the art and include many immortalized cell lines available from the American Type Culture Collection (ATCC), including but not limited to Chinese hamster ovary (CHO) cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive GCC binding properties.

A still further embodiment provides a method of producing an anti-GCC antibody molecule, e.g., a human or humanized antibody molecule, comprising maintaining the host cell comprising nucleic acids described herein, e.g., one or more nucleic acid sequence listed in Table 4 or 6, under conditions appropriate for expression of an immunoglobulin, whereby immunoglobulin chains, are expressed and an antibody molecule, e.g., a human or humanized antibody molecule that binds GCC, or a fragment or variant thereof, is produced. For example, methods of expression of antibody molecules include the use of host cells wherein a first recombinant nucleic acid molecule encoding an antibody molecule, e.g., a human or humanized antibody light chain, and a second recombinant nucleic acid molecule encoding an antibody molecule, e.g., a human or humanized antibody heavy chain, are comprised in a single expression vector. In other embodiments, they are in separate vectors. The method can further comprise the step of isolating or recovering the antibody, antigen-binding fragment of an antibody, antibody chain or antigen-binding fragment of an antibody chain, if desired.

For example, a nucleic acid molecule (i.e., one or more nucleic acid molecules) encoding the heavy and light chains of a human antibody that binds a GCC protein, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable non-human animal, in suitable culture media supplemented with appropriate salts, growth factors, antibiotics, nutritional supplements, etc.), whereby the encoded polypeptide(s) are produced. If desired, the encoded protein can be isolated or recovered (e.g., from the animal, the host cell, medium, milk). This process encompasses expression in a host cell of a transgenic non-human animal (see, e.g., WO 92/03918, GenPharm International) or plant.

Further, expression of antibodies of the invention (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning, Microdrop technology, or any other methods known in the art. The GS system is discussed in whole or part in connection with European Patent Nos. 0 216 846, 0 256 055, and 0 323 997 and European Patent Application No. 89303964.4.

In an exemplary system for recombinant expression of a modified antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

The antibodies, antigen-binding fragments, antibody chains and antigen-binding portions thereof described herein also can be produced in a suitable in vitro expression system, by chemical synthesis or by any other suitable method.

The anti-GCC antibodies described herein can be functionally linked by any suitable method (e.g., chemical coupling, genetic fusion, noncovalent association or otherwise) to one or more non-antibody molecular entities.

Fusion proteins can be produced in which an anti-GCC antibody molecule as described herein and a non-antibody moiety are components of a single continuous polypeptide chain. The non-antibody moiety can be located N-terminally, C-terminally, or internally, with respect to the antibody moiety. For example, some embodiments can be produced by the insertion of a nucleic acid encoding immunoglobulin sequences into a suitable expression vector, such as a pET vector (e.g., pET-15b, Novagen), a phage vector (e.g., pCNATAB 5 E, Pharmacia), or other vector, e.g., pRIT2T Protein A fusion vector, Pharmacia). The resulting construct can be expressed to produce antibody chains that comprise a non-antibody moiety (e.g., Histidine tag, E tag, or Protein A IgG binding domain). Fusion proteins can be isolated or recovered using any suitable technique, such as chromatography using a suitable affinity matrix (see, e.g., Current Protocols in Molecular Biology (Ausubel, F. M et al., eds., Vol. 2, Suppl. 26, pp. 16.4.1-16.7.8 (1991)).

The invention provides anti-GCC antibody molecules which are directed to and, in embodiments, are internalized into cells. They are capable of delivering therapeutic agents or detectable agents to or into cells expressing GCC, but not to or into cells where the target is not expressed. Thus, the invention also provides anti-GCC immunoconjugates comprising an anti-GCC antibody molecule as described herein, which is conjugated to a therapeutic agent or a detectable agent. In embodiments, the affinity for GCC of an anti-GCC immunoconjugate is at least 10, 25, 50, 75, 80, 90, or 95% of that for the unconjugated antibody. This can be determined using cell surface GCC or isolated GCC. In an embodiment the anti-GCC antibody molecule, e.g., an immunoconjugate, has an LD50, as determined by an assay described herein, of less than 1,000, 500, 250, 100, or 50 pM.

The anti-GCC antibody molecule can be modified to act as an immunoconjugate utilizing techniques that are known in the art. See e.g., Vitetta Immunol Today 14:252 (1993). See also U.S. Pat. No. 5,194,594. The preparation of radiolabeled antibodies can also be readily prepared utilizing techniques that are known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (U.S. Re. Pat. No. 35,500), U.S. Pat. Nos. 5,648, 471, and 5,697,902.

A variety of suitable linkers (e.g., heterobifunctional reagents for connecting an antibody molecule to a therapeutic agent or label) and methods for preparing immunoconjugates are known in the art. (See, for example, Chari et al., Cancer Research 52:127-131 (1992).) The linker can be cleavable, e.g., under physiological conditions, e.g., under intracellular conditions, such that cleavage of the linker releases the drug (therapeutic agent or label) in the intracellular environment. In other embodiments, the linker is not cleavable, and the drug is released, for example, by antibody degradation.

The linker can be bonded to a chemically reactive group on the antibody moiety, e.g., to a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues). The site to which the linker is bound can be a natural residue in the amino acid sequence of the antibody moiety or it can be introduced into the antibody moiety, e.g., by DNA recombinant technology (e.g., by introducing a cysteine or protease cleavage site in the amino acid sequence) or by protein biochemistry (e.g., reduction, pH adjustment or proteolysis).

One of the most commonly used non-specific methods of covalent attachment is the carbodiimide reaction to link a carboxy (or amino) group of a compound to amino (or carboxy) groups of the antibody molecule. Additionally, bifunctional agents such as dialdehydes or imidoesters have been used to link the amino group of a compound to amino groups of an antibody molecule. Also available for attachment of drugs to antibody molecules is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibody molecule. Other techniques are known to the skilled artisan and within the scope of the present invention.

In certain embodiments, an intermediate, which is the precursor of the linker (X), is reacted with the drug (Z) under appropriate conditions. In certain embodiments, reactive groups are used on the drug and/or the intermediate. The product of the reaction between the drug and the intermediate, or the derivatized drug, is subsequently reacted with the antibody molecule under appropriate conditions.

The immunoconjugate can be purified from reactants by employing methodologies well known to those of skill in the art, e.g., column chromatography (e.g., affinity chromatography, ion exchange chromatography, gel filtration, hydrophobic interaction chromatography), dialysis, diafiltration or precipitation. The immunoconjugate can be evaluated by employing methodologies well known to those skilled in the art, e.g., SDS-PAGE, mass spectroscopy, or capillary electrophoresis.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in GCC-expressing cells.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg Med. Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See for example U.S. Publication No. 20050238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of immunoconjugate, are cleaved when the immunoconjugate presents in an extracellular environment (e.g., in plasma). Whether a linker is not substantially sensitive to the extracellular environment can be determined, for example, by incubating with plasma the immunoconjugate for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent or label (Z). In yet other embodiments, the linker promotes cellular internalization when conjugated to both the Z moiety and the anti-GCC antibody molecule.

A variety of exemplary linkers that can be used with the present compositions and methods are described in WO 2004-010957, U.S. Publication No. 20060074008, U.S. Publication No. 20050238649, and U.S. Publication No. 20060024317 (each of which is incorporated by reference herein in its entirety and for all purposes).

Examples of linkers capable of being used to couple an antibody molecule to a therapeutic agent or label include, for example, maleimidocaproyl (mc); maleimidocaproyl-p-aminobenzylcarbamate; maleimidocaproyl-peptide-aminobenzylcarbamate linkers, e.g., maleimidocaproyl-L-phenylalanine-L-lysine-p-aminobenzylcarbamate and maleimidocaproyl-L-valine-L-citrulline-p-aminobenzylcarbamate (vc); N-succinimidyl 3-(2-pyridyldithio)proprionate (also known as N-succinimidyl 4-(2-pyridyldithio)pentanoate or SPP); 4-succinimidyl-oxycarbonyl-2-methyl-2-(2-pyridyldithio)-toluene (SMPT); N-succinimidyl 3-(2-pyridyldithio)propionate (SPDP); N-succinimidyl 4-(2-pyridyldithio)butyrate (SPDB); 2-iminothiolane; S-acetylsuccinic anhydride; disulfide benzyl carbamate; carbonate; hydrazone linkers; N-(.alpha.-Maleimidoacetoxy) succinimide ester; N-[4-(p-Azidosalicylamido)butyl]-3'-(2'-pyridyldithio)propionamide (AMAS); N-[.beta.-Maleimidopropyloxy]succinimide ester (BMPS); [N-.epsilon.-Maleimidocaproyloxy]succinimide ester (EMCS); N-[.gamma.-Maleimidobutyryloxy]succinimide ester (GMBS); Succinimidyl-4-[N-Maleimidomethyl]cyclohexane-1-carboxy-[6-amidocaproate] (LC-SMCC); Succinimidyl 6-(3-[2-pyridyldithio]-propionamido)hexanoate (LC-SPDP); m-Maleimidobenzoyl-N-hydroxysuccinimide ester (MBS); N-Succinimidyl[4-iodoacetyl]aminobenzoate (SIAB); Succinimidyl 4-[N-maleimidomethyl]cyclohexane-1-carboxylate (SMCC); N-Succinimidyl 3-[2-pyridyldithio]-propionamido (SPDP); [N-.epsilon.-Maleimidocaproyloxy]sulfosuccinimide ester (Sulfo-EMCS); N-[.gamma.-Maleimidobutyryloxy]sulfosuccinimide ester (Sulfo-GMBS); 4-Sulfosuccinimidyl-6-methyl-.alpha.-(2-pyridyldithio)toluamido]hexanoate-) (Sulfo-LC-SMPT); Sulfosuccinimidyl 6-(3'-[2-pyridyldithio]-propionamido) hexanoate (Sulfo-LC-SPDP); m-Maleimidobenzoyl-N-hydroxysulfosuccinimide ester (Sulfo-MBS); N-Sulfosuccinimidyl[4-iodoacetyl]aminobenzoate (Sulfo-SIAB); Sulfosuccinimidyl 4-[N-maleimidomethyl]cyclohexane-1-carboxylate (Sulfo-SMCC); Sulfosuccinimidyl 4-[p-maleimidophenyl]butyrate (Sulfo-SMPB); ethylene glycol-bis (succinic acid N-hydroxysuccinimide ester) (EGS); disuccinimidyl tartrate (DST); 1,4,7,10-tetraazacyclododecane-1,4,7,10-tetraacetic acid (DOTA); diethylenetriaminepentaacetic acid (DTPA); and thiourea linkers.

The variable Z moiety is a therapeutic agent or label. The therapeutic agent can be any agent capable of exerting a desired biological effect. In some embodiments, the therapeutic agent sensitizes the cell to a second therapeutic modality, e.g., a chemotherapeutic agent, radiation therapy, immunotherapy. In some embodiments, the therapeutic agent is a cytostatic or cytotoxic agent. Examples include, without limitation, antimetabolites (e.g., azathioprine, 6-mercaptopurine, 6-thioguanine, fludarabine, pentostatin, cladribine, 5-fluorouracil (5FU), floxuridine (FUDR), cytosine arabinoside (cytarabine), methotrexate, trimethoprim, pyrimethamine, pemetrexed); alkylating agents (e.g., cyclophosphamide, mechlorethamine, uramustine, melphalan, chlorambucil, thiotepa/chlorambucil, ifosfamide, carmustine, lomustine, streptozocin, busulfan, dibromomannitol, cisplatin, carboplatin, nedaplatin, oxaliplatin, satraplatin, triplatin tetranitrate, procarbazine, altretamine, dacarbazine, mitozolomide, temozolomide); anthracyclines (e.g., daunorubicin, doxorubicin, epirubicin, idarubicin, valrubicin); antibiotics (e.g., dactinomycin, bleomycin, mithramycin, anthramycin, streptozotocin, gramicidin D, mitomycins (e.g., mitomycin C), duocarmycins (e.g., CC-1065), calicheamicins); antimitotic agents (including, e.g., maytansinoids, auristatins, dolastatins, cryptophycins, vinca alkaloids (e.g., vincristine, vinblastine, vindesine, vinorelbine), taxanes (e.g., paclitaxel, docetaxel, or a novel taxane (see, e.g., International Patent Publication No. WO 01/38318, published May 31, 2001)), and colchicines; topoisomerase inhibitors (e.g., irinotecan, topotecan, amsacrine, etoposide, teniposide, mitoxantrone); and proteasome inhibitors (e.g., peptidyl boronic acids).

In some embodiments, the therapeutic agent is a maytansinoid. Maytansinoid compounds and methods for their conjugation to antibodies are described, for example, in Chari et al., Cancer Res., 52: 127-131 (1992); Widdison et al., J. Med. Chem. 49: 4392-4408 (2006); and U.S. Pat. Nos. 5,208,020 and 6,333,410.

Maytansinoid compounds that comprise a sulfhydryl group can be coupled to antibodies using a heterobifunctional linker that is connected to the maytansinoid compound by way of a thioether or disulfide linkage. In some such embodiments, the linker is coupled to an amino group on the antibody (e.g., a terminal amino group or the epsilon amino group of a lysine residue. In some embodiments, the heterobifunctional linker that is used to couple a maytansinoid compounds to an antibody is N-succinimidyl 3-(2-pyridyldithio)proprionate (also known as N-succinimidyl 4-(2-pyridyldithio)pentanoate, or SPP), 4-succinimidyl-oxycarbonyl-2-methyl-2-(2-pyridyldithio)-toluene (SMPT), N-succinimidyl 4[N-maleimidomethyl]cyclohexane-1-carboxylate (SMCC), N-succinimidyl 3-(2-pyridyldithio)propionate (SPDP); N-succinimidyl 4-(2-pyridyldithio)butyrate (SPDB), 2-iminothiolane, or S-acetylsuccinic anhydride.

In some other embodiments the therapeutic agent is a dolastatin. In some embodiments, the therapeutic agent is an auristatin, such as auristatin E (also known in the art as a derivative of dolastatin-10) or a derivative thereof.

Auristatin compounds and methods for their conjugation to antibodies are described, for example, in Doronina et al., Nature Biotech., 21: 778-784 (2003); Hamblett et al, Clin. Cancer Res., 10: 7063-7070 (2004); Carter and Senter, Cancer J., 14 154-169 (2008); U.S. Pat. Nos. 7,498,298, 7,091,186, 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414; U.S. Patent Publication Nos. 20090010945, 20060074008, 20080300192, 20050009751, 20050238649, and 20030083236; and International Patent Publication Nos. WO 04/010957 and WO 02/088172, each of which is incorporated by reference herein in its entirety and for all purposes.

The auristatin can be, for example, an ester formed between auristatin E and a keto acid. For example, auristatin E can be reacted with paraacetyl benzoic acid or benzoylvaleric acid to produce AEB and AEVB, respectively.

Auristatins have been shown to interfere with microtubule dynamics and nuclear and cellular division and have anticancer activity. Auristatins for use in the present invention bind tubulin and can exert a cytotoxic or cytostatic effect on a GCC-expressing cell line. Methods for determining whether a compound binds tubulin are known in the art. See, for example, Muller et al., Anal. Chem. 2006, 78, 4390-4397; Hamel et al., Molecular Pharmacology, 1995 47: 965-976; and Hamel et al., The Journal of Biological Chemistry, 1990 265:28, 17141-17149. For purposes of the present invention, the relative affinity of a compound to tubulin can be determined. Some preferred auristatins of the present invention bind tubulin with an affinity ranging from 10-fold lower (weaker affinity) than the binding affinity of MMAE to tubulin to 10-fold, 20-fold or even 100-fold higher (higher affinity) than the binding affinity of MMAE to tubulin.

There are a number of different assays, known in the art, that can be used for determining whether an auristatin or resultant immunoconjugate exerts a cytostatic or cytotoxic effect on a desired cell line. For example, the cytotoxic or cytostatic activity of an immunoconjugate can be measured by: exposing mammalian cells expressing a target protein of the immunoconjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the immunoconjugate.

For determining whether an immunoconjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 uCi of 3H-thymidine during the final 8 hours of the 72-hour period. The incorporation of 3H-thymidine into cells of the culture is measured in the presence and absence of the immunoconjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an immunoconjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan et al., 1990, J. Natl. Cancer Inst. 82:1107-12).

Alternatively, a tetrazolium salt, such as MTT or WST, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

The effects of immunoconjugates can be tested or validated in animal models. A number of established animal models of cancers are known to the skilled artisan, any of which can be used to assay the efficacy of an immunoconjugate. Non-limiting examples of such models are described infra. Moreover, small animal models to examine the in vivo efficacies of immunoconjugates can be created by implanting human tumor cell lines into appropriate immunodeficient rodent strains, e.g., athymic nude mice or SCID mice.

In some embodiments, the auristatin molecule is linked to a cysteine moiety on the antibody molecule by way of a linker containing a maleimide moiety, e.g., a maleimidocaproyl moiety.

In some embodiments, the auristatin molecule is coupled to the antibody molecule using a heterobifunctional linker that is connected to a hydroxyl group on the auristatin molecule. In some such embodiments, the linker comprises a hydrazone. In some embodiments, the linker is a hydrazone compound formed by reaction of maleimidocaproyl-hydrazide and a ketocarboxylic acid, e.g., 5-benzoylvaleric acid. In particular embodiments, the linker is (Z)-6-(2-(6-(2,5-dioxo-2,5-dihydro-1H-pyrrol-1-yl)-hexanoyl)hydrazono)-6-phenylhexanoic acid.

In some other embodiments the auristatin molecule is coupled to the antibody using a heterobifunctional linker that is connected to a monomethyl amino group on the auristatin molecule. In some embodiments, the linker comprises a cleavable moiety, e.g., a peptide moiety, and a self-immolative p-aminobenzylcarbamate spacer. Exemplary linkers include maleimidocaproyl (mc), maleimidocaproyl-L-phenylalanine-L-lysine-p-aminobenzylcarbamate, and maleimidocaproyl-L-valine-L-citrulline-p-aminobenzylcarbamate (vc).

The immunoconjugates disclosed herein can be used for modifying a given biological response. The therapeutic agent is not to be construed as limited to classical chemical therapeutic agents. For example, the therapeutic agent may be a nucleic acid, protein, or polypeptide possessing a desired biological activity. For example, the antibody molecule can be conjugated to an antisense molecule, an siRNA molecule, shRNA molecule or miRNA molecule that can interfere with expression of a gene, thereby producing a desired biological effect.

Proteins and polypeptides that can be conjugated to the antibody molecules of the invention include, for example, toxins and components thereof, such as abrin, abrin A chain, ricin, ricin A chain, modeccin, modeccin A chain, alpha-sarcin, exotoxin A (from *Pseudomonas aeruginosa*), PE38 (truncated *pseudomonas* exotoxin), gelonin, diphtheria toxin, diphtheria toxin A fragment, certain *Aleurites fordii* proteins, certain *Dianthus caryophyllus* proteins (e.g., dianthin 30 and dianthin 32), certain *Phytolacca Americana* proteins (e.g., PAP, PAPII, and PAP-S), certain *Saponaria officinlis* proteins (e.g., saporin 6), *Momordica charantia* inhibitor, curcin, crotin, mitogillin, restrictocin, phenomycin, and enomycin; proteins to engage the immune system at the tumor or induce an effector function at the tumor, such as tumor necrosis factor, interferon, nerve growth factor, platelet derived growth factor, and tissue plasminogen activator; and biological response modifiers such as, for example, cytokines and lymphokines (e.g., interleukin-1 ("IL-1"), interleukin-2 ("IL-2"), interleukin-6 ("IL-6"), granulocyte macrophase colony stimulating factor ("GM-CSF"), and granulocyte colony stimulating factor ("G-CSF")), and other growth factors.

The antibodies of the invention can also be conjugated or fused to viral surface proteins present on viral particles. For example, a single-chain anti-GCC antibody of the present invention could be fused (e.g., to form a fusion protein) to a viral surface protein. Alternatively, a whole anti-GCC antibody of the present invention, or a fragment thereof, could be chemically conjugated (e.g., via a chemical linker) to a viral surface protein. Preferably, the virus is one that fuses with endocytic membranes, e.g., an influenza virus, such that the virus is internalized along with the anti-GCC antibody and thereby infects GCC-expressing cells. The virus can be genetically engineered as a cellular toxin. For example, the virus could express or induce the expression of genes that are toxic to cells, e.g., cell death promoting genes. Preferably, such viruses would be incapable of viral replication.

An anti-GCC antibody molecule described herein can also be conjugated to a prodrug or prodrug activator. In a method to kill or suppress tumor cells, a first anti-GCC antibody molecule of the invention is conjugated with a prodrug that is activated only when in close proximity with a prodrug activator. The prodrug activator is conjugated with a second antibody molecule, preferably one that binds to a non-competing site on the GCC molecule. Whether two antibodies bind to competing or non-competing binding sites can be determined by conventional competitive binding assays. Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," (1996) Cancer Research, 56:3287-3292.

Therapeutically active radioisotopes can also be coupled to anti-GCC antibodies, or antigen binding fragments, or derivatives thereof. Radioactive isotopes can be used in diagnostic or therapeutic applications. Radioactive isotopes that can be coupled to the anti-GCC antibodies include, but are not limited to alpha-, beta-, or gamma-emitters, or beta- and gamma-emitters. See, e.g., S. E. Order, "Analysis, Results, and Future Prospective of the Therapeutic Use of Radiolabeled Antibody in Cancer Therapy," Monoclonal Antibodies for Cancer Detection and Therapy, R. W. Baldwin et al. (eds.), pp 303-316 (Academic Press 1985. Such radioactive isotopes include, but are not limited to copper (64Cu), iodine (131I or 125I), yttrium (90Y), lutetium (177Lu), actinium (225Ac), praseodymium, astatine (211At) rhenium (186Re), bismuth (212Bi or 213Bi), indium (111I), technetium (99 mTc), phosphorus (32P), rhodium (188Rh), sulfur (35S), carbon (14C), tritium (3H), chromium (51Cr), chlorine (36Cl), cobalt (57Co or 58Co), iron (59Fe), selenium (75Se), or gallium (67Ga). Radioisotopes useful as therapeutic agents include yttrium (90Y), lutetium (177Lu), actinium (225Ac), praseodymium, astatine (211At), rhenium (186Re), bismuth (212Bi or 213Bi), and rhodium (188Rh). Radioisotopes useful as labels, e.g., for use in diagnostics, include iodine (131O or 125I), indium (111In), technetium (99 mTc), phosphorus (32P), carbon (14C), and tritium (3H), or one or more of the therapeutic isotopes listed above.

Radioimmunotherapy (RIT) using antibodies labeled with 131I, 90Y, and 177Lu is under intense clinical investigation. There are significant differences in the physical characteristics of these three nuclides and as a result, the choice of radionuclide can be important in order to deliver maximum radiation dose to the tumor. The higher beta energy particles of .sup.90Y may be good for bulky tumors, but it may not be necessary for small tumors and especially bone metastases. The relatively low energy beta particles of 131I are ideal, but in vivo dehalogenation of radioiodinated molecules is a major disadvantage for internalizing antibody. In contrast, 177Lu has low energy beta particle with only 0.2-0.3 mm range and delivers much lower radiation dose to bone marrow compared to 90Y. In addition, due to longer physical half-life (compared to 90Y), the tumor residence times are higher. As a result, higher activities (more mCi amounts) of 177Lu labeled agents can be administered with comparatively less radiation dose to marrow. There have been several clinical studies investigating the use of 177Lu labeled antibodies in the treatment of various cancers. (Mulligan T et al. Clin Cancer Res. 1: 1447-1454 (1995); Meredith R F, et al. J Nucl Med 37:1491-1496 (1996); Alvarez R D, et al. Gynecologic Oncology 65: 94-101 (1997)).

Useful detectable agents with which an antibody or an antibody portion of the invention may be derivatized (or labeled) include fluorescent compounds, various enzymes, prosthetic groups, luminescent materials, bioluminescent materials, fluorescent emitting metal atoms, e.g., europium (Eu), and other anthanides, and radioactive materials (described above). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, .beta.-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

In another aspect, the invention features compositions, e.g., pharmaceutically acceptable compositions, which include an anti-GCC antibody molecule or immunoconjugate thereof, as described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). The pharmaceutical composition can include one or more additional excipients, e.g., salts, buffers, tonicity modifiers, lyoprotectants, nonionic detergents, surfactants, and preservatives.

The compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Some typical compositions are in the form of injectable or infusible solutions, intended for parenteral administration (e.g., intravenous, subcutaneous, intraperitoneal, intramuscular). In some embodiments, the antibody is administered by intravenous infusion or injection. In other embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In some embodiments, the pharmaceutical composition is sterile and stable under the conditions of manufacture and storage. The composition can be formulated as a solution, microemulsion, dispersion, liposome, microsphere, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by sterilization, e.g., by filtration. Generally, dispersions are prepared by incorporating the active compound into a sterile vehicle that contains a basic dispersion medium and the required other ingredients from those enumerated above. In the case of sterile powders for the preparation of sterile injectable solutions, the provided methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antigen binding fragments of the present invention can be administered by a variety of methods known in the art, although for many therapeutic applications, the route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an anti-GCC antibody molecule or immunoconjugate described herein may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixirs, suspensions, syrups, wafers, and the like. To administer an antibody or an antibody fragment of the invention by other than parenteral administration, it may be necessary to coat the compound with, or co-administer the compound with, a material to prevent its inactivation.

Therapeutic compositions can be administered with medical devices known in the art. For example, pharmaceutical preparations can be disposed within a device, e.g., an air- or liquid-tight container, which contains one or more dosages. Examples of delivery devices include, without limitation, vials, cannulas, needles, drip bags, and lines. The invention also provides methods of placing an antibody molecule or immunoconjugate described herein into such a device.

In some embodiments, the invention provides an anti-GCC antibody molecule or immunoconjugate described herein, which is formulated in a liposome composition. In some embodiments, the liposome is coated with antibody molecule. In some such embodiments, the liposome is filled with a therapeutic agent. Liposomic delivery can allow for the delivery of an agent, e.g., a therapeutic agent, that is not linked to the antibody. This approach can be used to deliver an agent, e.g., a therapeutic agent, that is not amenable to cross-linking to the antibody molecule or an agent, e.g., a therapeutic agent, which is to be sequestered, or which contact with non-target cells should be minimized. In particular embodiments, the liposome is filled with a cytostatic or cytotoxic agent. In certain particular embodiments, the therapeutic agent is selected from the group consisting of maytansinoids, an auristatins, dolastatins, duocarmycins, cryptophycins, taxanes, DNA alkylating agents calicheamicins, and derivatives of the foregoing. In other embodiments, the liposome is filled with nucleic acid sequence comprising RNA interference molecules, e.g., antisense molecules, siRNA, hsRNA or miRNA molecules, which are capable of diminishing GCC expression or the expression of another gene, e.g., an oncogene, in cells expressing GCC. In some other embodiments, the liposome is coated or filled with an immunoconjugate comprising an anti-GCC antibody molecule and a therapeutic agent or label.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. The term "dosage unit form," as used herein, refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or an antigen binding fragment of the invention is 0.1-20 mg/kg, or 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective" amount of an antibody or an antigen binding fragment of the invention. A "therapeutically effective" amount refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter (e.g., tumor growth rate) in treated subjects by at least about 20%, at least about 40%, at least about 60%, and in some embodiments at least about 80%, relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

Also within the scope of the invention are kits comprising an anti-GCC antibody molecule or immunoconjugate as described herein. Further included are kits comprising liposome compositions comprising an anti-GCC antibody molecule or immunoconjugate. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject. Instructions for use can include instructions for diagnostic applications of the anti-GCC antibody molecule or immunoconjugate to detect GCC, in vitro, e.g., in a sample, e.g., a biopsy or cells from a patient having a cancer, or in vivo. The instructions can include guidance for therapeutic application including suggested dosages and/or modes of administration, e.g., in a patient with a cancer (e.g., a cancer of gastrointestinal origin, such as, for example, colon cancer, stomach cancer, esophageal cancer). Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. In some applications the antibody will be reacted with other components, e.g., a chelator or a label or therapeutic agent, e.g., a radioisotope, e.g., yttrium or lutetium. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-GCC antibody molecules or immunoconjugates, formulated as appropriate, in one or more separate pharmaceutical preparations.

The kit can further contain a radioprotectant. The radiolytic nature of isotopes, e.g., $^{90}$Yttrium (90Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody. The formulation buffer of the present invention may include a radioprotectant such as human serum albumin (HSA) or ascorbate, which minimize radiolysis due to yttrium or other strong radionuclides. Other radioprotectants are known in the art and can also be used in the formulation buffer of the present invention, i.e., free radical scavengers.

A provided kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation buffer, and administered directly to the patient with or without further purification. The chelator-conjugated antibody may be supplied in lyophilized form.

The anti-GCC antibody molecules described herein have in vitro and in vivo diagnostic, prognostic, imaging, therapeutic and prophylactic utilities. For example, these antibody molecules can be administered to cells in culture, e.g. in vitro or ex vivo, or administered in a subject, e.g., in vivo, to treat, prevent, and/or diagnose a variety of disorders.

The antibody molecules, immunoconjugates, and fusion proteins described herein can be used can modulate an activity or function of a GCC protein, such as ligand binding (e.g., binding of ST or guanylin), GCC-mediated signal transduction, maintenance of intestinal fluid, electrolyte homeostasis, intracellular calcium release (calcium flux), cell differentiation, cell proliferation, or cell activation.

In one aspect, the invention features a method of killing, inhibiting or modulating the growth of, or interfering with the metabolism of, a GCC-expressing cell. In one embodiment, the invention provides a method of inhibiting GCC-mediated cell signaling or a method of killing a cell. The method may be used with any cell or tissue which expresses GCC, such as a cancerous cell (e.g., a cell from a cancer of the gastrointestinal system, such as, for example, a cancer of the colon, stomach, or esophagus, or a pancreatic cell), or a metastatic lesion. Nonlimiting examples of GCC-expressing cells include T84 human colonic adenocarcinoma cells, fresh or frozen colonic tumor cells, and cells comprising a recombinant nucleic acid encoding GCC or a portion thereof.

Methods of the invention include the steps of contacting the cell with an anti-GCC antibody molecule or immunoconjugate thereof, as described herein, in an effective amount, i.e., amount sufficient to inhibit GCC-mediated cell signaling or an amount sufficient to kill the cell. The method can be used on cells in culture, e.g. in vitro, in vivo, ex vivo, or in situ. For example, cells that express GCC (e.g., cells collected by biopsy of a tumor or metastatic lesion; cells from an established cancer cell line; or recombinant cells), can be cultured in vitro in culture medium and the contacting step can be effected by adding the anti-GCC antibody molecule or immunoconjugate to the culture medium. In methods of killing a cell, the method comprises using a naked anti-GCC antibody molecule, or an immunoconjugate comprising an anti-GCC antibody molecule and a cytotoxic agent. The method will result in killing of cells expressing GCC, including in particular tumor cells expressing GCC (e.g., colonic tumor cells).

Antibodies may be linked to a cytotoxic moiety or a moiety for cell imaging. Antibodies which do not internalize can be used for diagnostic purposes or therapeutic methods using naked antibody designed to elicit an antibody-dependent cell-mediated cytotoxic response, or perhaps for liposome delivery methods.

Anti-GCC antibody molecules of the present invention bind to extracellular domains of GCC or portions thereof in cells expressing the antigen. As a result, when practicing the methods of the present invention to kill, suppress, or detect cancerous cells, the antibodies or antigen binding fragments, bind to all such cells, not only to cells which are fixed or cells whose intracellular antigenic domains are otherwise exposed to the extracellular environment. Consequently, binding of the antibodies or antigen binding fragments, is concentrated in areas where there are cells expressing GCC, irrespective of whether these cells are fixed or unfixed, viable or necrotic. Additionally or alternatively, the anti- GCC antibody molecules, bind to and are internalized with GCC upon binding cells expressing the antigen.

The method also can be performed on cells present in a subject, as part of an in vivo protocol. In one embodiment, the subject is a human subject. Alternatively, the subject can be a mammal expressing a GCC antigen with which an anti-GCC antibody molecule disclosed herein cross-reacts. An anti-GCC antibody molecule or immunoconjugate thereof can be administered to a human subject for therapeutic purposes. An anti-GCC antibody molecule or immunoconjugate also can be administered to a non-human mammal expressing the GCC-like antigen with which the antibody cross-reacts (e.g., a primate, pig or mouse) for veterinary purposes or as an animal model of human disease. Animal models may be useful for evaluating the therapeutic efficacy of antibodies of the invention (e.g., testing of dosages and time courses of administration). For in vivo embodiments, the contacting step is effected in a subject and includes administering an anti-GCC antibody molecule or immunoconjugate thereof to the subject under conditions effective to permit both binding of the antibody molecule to the extracellular domain of GCC expressed on the cell, and the treating of the cell.

In one embodiment, the invention provides a method of treating cancer by administering an anti-GCC antibody molecule or an immunoconjugate comprising an anti-GCC antibody molecule and a cytotoxic agent to a patient in need of such treatment. The method can be used for the treatment of any cancerous disorder which includes at least some cells that express the GCC antigen. As used herein, the term "cancer" is meant to include all types of cancerous growths or oncogenic processes, metastatic tissues or malignantly transformed cells, tissues, or organs, irrespective of histopathologic type or stage of invasiveness. The terms "cancer" and "tumor" may be used interchangeably (e.g., when used in the context of treatment methods, "treatment of a cancer" and "treatment of a tumor" have the same meaning).

In embodiments, the treatment is sufficient to reduce or inhibit the growth of the subject's tumor, reduce the number or size of metastatic lesions, reduce tumor load, reduce primary tumor load, reduce invasiveness, prolong survival time, or maintain or improve the quality of life.

The cancer to be treated may be a cancer of the gastrointestinal system (e.g., colorectal cancer, esophageal cancer, or stomach cancer). In one embodiment, the cancer is a colorectal cancer, e.g., colorectal adenocarcinoma, colorectal leiomyosarcoma, colorectal lymphoma, colorectal melanoma, or a colorectal neuroendocrine tumor. In a particular embodiment, the cancer is metastatic colon cancer. In another embodiment, the cancer is a stomach cancer (e.g., gastric adenocarcinoma, lymphoma, or sarcoma), or metastasis thereof. In another embodiment, the cancer is an esophageal cancer (e.g., a squamous cell carcinoma or adenocarcinoma of the esophagus). The method can be useful in treating a relevant disorder at any stage or subclassification. For example, method can be used to treat early or late stage colon cancer, or colon cancer of any of stages 0, I, IIA, IIB, IIIA, IIIB, IIIC, and IV.

In some embodiments, the method for treating cancer (e.g., a cancer described herein, e.g., colorectal, esophageal, or stomach cancer) comprises administering to a patient in need of such treatment a naked anti-GCC antibody molecule described herein. In other embodiments, the method comprises administering an immunoconjugate comprising an anti-GCC antibody molecule described herein and a cytotoxic agent.

Methods of administering antibody molecules and immunoconjugates are described above. Suitable dosages of the molecules used will depend on the age and weight of the subject and the particular compound used.

In some embodiments, the anti-GCC antibody molecule or immunoconjugate is administered in treatment cycles. A "treatment cycle" consists of a treatment period, during which the anti-GCC antibody molecule or immunoconjugate is administered as described above, followed by a rest period, during which no anti-GCC antibody molecule or immunoconjugate is administered. The treatment cycle can be repeated as necessary to achieve the desired effect.

The anti-GCC antibodies described herein (e.g., naked anti-GCC antibody molecules or immunoconjugates comprising an anti-GCC antibody molecule and a therapeutic agent) may be used in combination with other therapies. For example, the combination therapy can include a composition of the present invention co-formulated with, and/or co-administered with, one or more additional therapeutic agents, e.g., one or more anti-cancer agents, e.g., cytotoxic or cytostatic agents, hormone treatment, vaccines, and/or other immunotherapies. In other embodiments, the anti-GCC antibodies are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the anti-GCC antibody molecule or immunoconjugate thereof is used in combination with a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-.kappa.B inhibitors, including inhibitors of I.kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, overexpressed or activated in cancers, the inhibition of which downregulates cell replication.

The selection of therapeutic agent(s) or treatment modality to be combined with an anti-GCC antibody molecule or immunoconjugate of the invention will depend on the disorder to be treated. The additional agent(s) or treatment modality may include, for example, standard approved therapies for the indication being treated. For example, when the anti-GCC antibody molecule or immunoconjugate thereof is used to treat colon cancer, it may be used in combination with, e.g., surgery; radiation therapy; 5-fluorouricil (5-FU), capecitibine, leucovorin, irinotecan, oxaliplatin, bevacizumab, cetuximab, panitumum, or combinations thereof (e.g., oxaliplatin/capecitibine (XELOX), 5-fluorouricil/leucovorin/-oxaliplatin (FOLFOX), 5-fluorouricil/leucovorin/irinotecan (FOLFIRI), FOLFOX plus bevacizumab, or FOLFIRI plus bevacizumab).

In another aspect, the invention features the use of an anti-GCC antibody molecule or immunoconjugate as described herein in the manufacture of a medicament. In an embodiment, the medicament is for treating cancer, e.g., a gastrointestinal cancer.

Anti-GCC antibodies and immunoconjugates described herein can be used to detect the presence of GCC, e.g., to detect the presence of GCC in a biological sample, or to detect the presence or distribution of GCC in a subject. The term "detecting" as used herein encompasses quantitative or qualitative detection. Detecting GCC or GCC protein, as used herein, means detecting intact GCC protein or detecting a portion of the GCC protein that comprises the epitope to which the anti-GCC antibody molecule binds.

Accordingly, in another aspect, the invention features, a method of detecting GCC protein, e.g., detecting a GCC expressing cell or tissue, e.g., a tumor cell, or a tumor having cells, that express GCC. The method comprises: contacting a material, e.g., a cell or tissue, e.g., a sample of a tumor which expresses GCC, with an anti-GCC antibody molecule, e.g., an anti-GCC antibody molecule described herein, under conditions which allow formation of a complex between the anti-GCC antibody molecule and GCC protein; and detecting formation of a complex between antibody molecule and GCC protein, to thereby detect the presence of GCC protein, e.g., to detect a GCC expressing cell or tumor.

In an embodiment the anti-GCC antibody molecule is an immunoconjugate comprising a detectable label.

In certain embodiments, the tissues include normal and/or cancerous tissues that express GCC at higher levels relative to other tissues, for example other tissue such as B cells and/or B cell associated tissues.

Methods of detection described herein, whether in vitro or in vivo, can be used to evaluate a subject. In an embodiment the method is performed in vivo, and can be used, e.g., for imaging, staging, evaluation or diagnosis of a patient. In certain embodiments, the disorder is a cell proliferative disorder, such as a cancer or a tumor, e.g., colon cancer.

Thus, in another aspect, the invention provides, a method for detecting the presence of GCC protein in vitro (e.g., in a biological sample, such as a tissue biopsy, e.g., from a tumor tissue, from a subject) or in vivo (e.g., by in vivo imaging in a subject). The method comprises: (i) contacting a sample with an anti-GCC antibody molecule or immunoconjugate thereof, or administering to a subject, an anti-GCC antibody molecule or immunoconjugate thereof; and (ii) detecting formation of a complex between the anti-GCC antibody molecule and GCC protein. Complex formation is indicative of the presence or level of GCC.

In embodiments the level of complex detected in the sample or subject is compared with a reference value, e.g., a value for complex formation or level of GCC. In an embodiment a level of GCC which exceeds a reference value is indicative of a GCC-mediated disorder.

In an embodiment the method comprises contacting a reference sample, e.g., a control sample (e.g., a control biological sample, such as plasma, tissue, biopsy) or a control subject) with an anti-GCC antibody molecule or immunoconjugate thereof and comparing the level of complex detected therein with the level detected in the sample or subject.

In certain embodiments, a test cell or tissue is obtained from an individual suspected of having a disorder associated with increased expression of GCC.

In an embodiment the level of GCC, in a sample from the subject, or in the subject, is compared with a reference level, e.g., the level of GCC in a control material, e.g., a normal cell of the same tissue origin as the subject's cell or a cell having GCC at levels comparable to such a normal cell. The method can comprise, e.g., responsive to the detected level of GCC, providing a diagnosis, a prognosis, an evaluation of the efficacy of treatment, or the staging of a disorder. A higher level of GCC in the sample or subject, as compared to the control material, indicates the presence of a disorder associated with increased expression of GCC. A higher level of GCC in the sample or subject, as compared to the control material, can also indicate, the relative lack of efficacy of a treatment, a relatively poorer prognosis, or a later stage of disease. The level of GCC can also be used to evaluate or select future treatment, e.g., the need for more or less aggressive treatment, or the need to switch from one treatment regimen to another.

The level of GCC can also be used to select or evaluate patients. E.g., in embodiments patients whose tumor cells express high amounts of GCC on their surfaces would be considered good candidates for treatment with toxin-conjugated anti-GCC antibody molecules. In embodiments patients whose tumor cells express low amounts of GCC on their surfaces would not be as good candidates for this or might be candidates for combining the anti-GCC antibody molecule with an additional treatment method, or be candidates for naked antibody therapy. In another example, the dose of the toxin-conjugated anti-GCC antibody molecule could be adjusted to reflect the number of GCC molecules expressed on the surfaces of tumor cells. Patients with high numbers of GCC molecules on their tumor cell surfaces might be treated with lower doses than patients with low numbers of GCC molecules. Detecting the presence of GCC-expressing tumor cells in vivo can allow identification of tissues into the primary GCC-expressing tumor has metastasized. Knowledge of which tissues have metastases can lead to targeted application of tumor therapy.

As discussed above, the antibody molecules described herein permit assessment of the presence of a GCC protein in normal versus neoplastic tissues, through which the presence or severity of disease, disease progress and/or the efficacy of therapy can be assessed. For example, therapy can be monitored and efficacy assessed. In one example, a GCC protein can be detected and/or measured in a first sample obtained from a subject having an inflammatory disease and therapy can be initiated. Later, a second sample can be obtained from the subject and GCC protein in the sample can be detected and/or measured. A decrease in the quantity of GCC protein detected or measured in the second sample can be indicative of therapeutic efficacy.

Exemplary cell proliferative disorders that may be evaluated, e.g., diagnosed, using an antibody disclosed herein include a proliferative disorder including, but not limited to, colon cancer, stomach cancer, esophageal cancer.

In certain embodiments, a method, such as those described above, comprises detecting binding of an anti-GCC antibody to GCC expressed on the surface of a cell or in a membrane preparation obtained from a cell expressing GCC on its surface. In certain embodiments, the method comprises contacting a cell with an anti-GCC antibody under conditions permissive for binding of the anti-GCC antibody to GCC, and detecting whether a complex is formed between the anti-GCC antibody and GCC on the cell surface. An exemplary assay for detecting binding of an anti-GCC antibody to GCC expressed on the surface of a cell is a "FACS" assay.

Exemplary samples for methods described herein comprise tissue or body fluid, such as an inflammatory exudate, blood, serum, bowel fluid, stool sample, or biopsy. In one example, a sample (e.g., tissue and/or body fluid) can be obtained from an individual and a suitable immunological method can be used to detect and/or measure GCC protein expression. Suitable immunological methods for detecting or measuring GCC protein expression include enzyme-linked immunosorbent assays (ELISA), radioimmunoassay, immunohistology, flow cytometry, and the like.

Anti-GCC antibody molecules used in methods described herein, e.g., in the in vivo and in vitro detection, e.g., diagnostic, staging, or imaging methods, can be directly or indirectly labeled with a detectable substance to facilitate detection of the bound or unbound binding agent. Suitable detectable substances include various biologically active enzymes, ligands, prosthetic groups, fluorescent materials, luminescent materials, chemiluminescent materials, bioluminescent materials, chromophoric materials, electron dense materials, paramagnetic (e.g., nuclear magnetic resonance active) materials, and radioactive materials. In some embodiments, the anti-GCC antibody molecule is coupled to a radioactive ion, e.g., indium (111In), iodine (131I or 125I), yttrium (90Y), lutetium (177Lu), actinium (225Ac), bismuth (212Bi or 213Bi), sulfur (35S), carbon (14C), tritium (3H), rhodium (188Rh), technetium (99 mTc), praseodymium, or phosphorous (32P); or a positron-emitting radionuclide, e.g., carbon-11 (11C) potassium-40 (40K), nitrogen-13 (13N), oxygen-15 (15O), fluorine-18 (18F), and iodine-121 (121I).

Exemplary labels include fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, and 2,3-dihydrophthalazinediones Other exemplary labels include horseradish peroxidase (HRP), alkaline phosphatase, galactosidase, glucoamylase, lysozyme, saccharide oxidases, e.g., glucose oxidase, galactose oxidase, and glucose 6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Fluorophore and chromophore labeled antibody molecules can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescent compounds and chromophores are described by Stryer Science, 162:526 (1968) and Brand, L. et al. Annual Review of Biochemistry, 41:843-868 (1972). The antibodies can be labeled with fluorescent chromophore groups by conventional procedures such as those disclosed in U.S. Pat. Nos. 3,940,475, 4,289,747, and 4,376,110.

One group of fluorescers having a number of the desirable properties described above is the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the alpha or beta position.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

Certain other methods can be used to detect binding of anti-GCC antibodies to GCC. Such methods include, but are not limited to, antigen-binding assays that are known in the art, such as western blots, radioimmunoassays, ELISA (enzyme linked immunosorbent assay), "sandwich" Immunoassays, immunoprecipitation assays, fluorescent immunoassays, protein A immunoassays, and immunohistochemistry (IHC).

Complex formation between the anti-GCC antibody molecule and GCC can be detected by measuring or visualizing either the antibody (or antibody fragment) bound to the GCC antigen or unbound antibody molecule. Conventional detection assays can be used, e.g., western blots, radioimmunoassays, ELISA (enzyme linked immunosorbent assay), "sandwich" immunoassays, immunoprecipitation assays, fluorescent immunoassays, protein A immunoassays, and immunohistochemistry (IHC) or radioimmunoassay (RIA).

Alternative to labeling the anti-GCC antibody molecule, the presence of GCC can be assayed in a sample by a competition immunoassay utilizing standards labeled with a detectable substance and an unlabeled anti-GCC antibody molecule. In this assay, the biological sample, the labeled standards and the GCC binding agent are combined and the amount of labeled standard bound to the unlabeled antibody is determined. The amount of GCC in the sample is inversely proportional to the amount of labeled standard bound to the GCC binding agent.

It is also possible to directly detect GCC to anti-GCC antibody molecule complex formation without further manipulation or labeling of either component (GCC or antibody molecule), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the acceptor' molecule label in the assay should be maximal. An FET binding event can be conveniently measured through standard fluorometric detection means well known in the art (e.g., using a fluorimeter).

In another example, determination of the ability of an antibody molecule to recognize GCC can be accomplished without labeling either assay component (GCC or antibody molecule) by utilizing a technology such as real-time Biomolecular Interaction Analysis (BIA) (see, e.g., Sjolander, S, and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In still another embodiment, the invention provides a method for detecting the presence of GCC-expressing tumor tissues in vivo. The method includes (i) administering to a subject (e.g., a patient having a cancer) an anti-GCC antibody or antigen binding fragment thereof, preferably a antibody or antigen binding fragment thereof conjugated to a detectable label or marker; (ii) exposing the subject to a means for detecting said detectable label or marker to the GCC-expressing tissues or cells.

Examples of labels useful for diagnostic imaging in accordance with the present invention are radiolabels such as 131I, 111In, 68Ga, 99mTc, 32P, 125I, 3H, 14C, and 188Rh, fluorescent labels such as fluorescein and rhodamine, nuclear magnetic resonance active labels, positron emitting isotopes detectable by a single photon emission computed tomography ("SPECT") detector or positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, see Wensel and Meares (1983) Radioimmunoimaging and Radioimmunotherapy, Elsevier, N.Y., for techniques relating to the radiolabeling of antibodies. See also, D. Colcher et al. Meth. Enzymol. 121: 802-816 (1986.

In the case of a radiolabeled antibody, the antibody is administered to the patient, is localized to the tumor bearing the antigen with which the antibody reacts, and is detected or "imaged" in vivo using known techniques such as radionuclear scanning using e.g., a gamma camera or emission tomography or computed tomography. See e.g., A. R. Bradwell et al., "Developments in Antibody Imaging", Monoclonal Antibodies for Cancer Detection and Therapy, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., 11C, 18F, 15O, and 13N).

In other embodiments, the invention provides methods for determining the dose, e.g., radiation dose, that different tissues are exposed to when a subject, e.g., a human subject, is administered an anti-GCC antibody molecule that is conjugated to a radioactive isotope. The method includes: (i) administering an anti-GCC antibody molecule as described herein, e.g., a anti-GCC antibody molecule, that is labeled with a radioactive isotope to a subject; (ii) measuring the amount of radioactive isotope located in different tissues, e.g., tumor, or blood, at various time points until some or all of the radioactive isotope has been eliminated from the body of the subject; and (iii) calculating the total dose of radiation received by each tissue analyzed. The measurements can be taken at scheduled time points, e.g., day 1, 2, 3, 5, 7, and 12, following administration (at day 0) of the radioactively labeled anti-GCC antibody molecule to the subject. The concentration of radioisotope present in a given tissue, integrated over time, and multiplied by the specific activity of the radioisotope can be used to calculate the dose that a given tissue receives. Pharmacological information generated using anti-GCC antibody molecules labeled with one radioactive isotope, e.g., a gamma-emitter, e.g., 111In can be used to calculate the expected dose that the same tissue would receive from a different radioactive isotope which cannot be easily measured, e.g., a beta-emitter, e.g., 90Y.

The invention claimed is:

1. A method of treating a subject who has been diagnosed as having cancer comprising cancer cells that express guanylyl cyclase C (GCC), the method comprising administering to said subject a therapeutically effective amount of T cells that express a chimeric antigen receptor comprising a light chain variable region and a heavy chain variable region of an anti-GCC antibody molecule, the chimeric antigen receptor comprising: heavy chain variable region Amino Acid Sequence SEQ ID NO:3 from anti-GCC antibody MS20, and light chain variable region Amino Acid Sequence SEQ ID NO:4 from anti-GCC antibody MS20; wherein the chimeric antigen receptor binds to human GCC.

2. The method of claim 1, wherein the cancer is metastatic colorectal cancer, primary and/or metastatic esophageal cancer, or primary and/or metastatic stomach cancer.

3. The method of claim 1, wherein the cancer is metastatic colorectal cancer.

4. The method of claim 1, wherein the cancer is primary and/or metastatic esophageal.

5. The method of claim 1, wherein the cancer is primary and/or metastatic stomach cancer.

* * * * *